United States Patent
Grubbs et al.

(10) Patent No.: US 10,166,731 B2
(45) Date of Patent: ***Jan. 1, 2019

(54) METHOD FOR MODIFYING POWER OF LIGHT ADJUSTABLE LENS

(71) Applicant: RxSight, Inc., Aliso Viejo, CA (US)

(72) Inventors: Robert H. Grubbs, Pasadena, CA (US); Christian A. Sandstedt, Pasadena, CA (US)

(73) Assignee: RxSight, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/959,263

(22) Filed: Apr. 22, 2018

(65) Prior Publication Data

US 2018/0244003 A1    Aug. 30, 2018

Related U.S. Application Data

(63) Continuation of application No. 15/159,909, filed on May 20, 2016, now Pat. No. 9,950,482.

(60) Provisional application No. 62/164,413, filed on May 20, 2015.

(51) Int. Cl.
| | |
|---|---|
| *A61F 2/16* | (2006.01) |
| *B29D 11/00* | (2006.01) |
| *B29D 11/02* | (2006.01) |
| *B29K 683/00* | (2006.01) |

(52) U.S. Cl.
CPC ...... *B29D 11/00461* (2013.01); *A61F 2/1627* (2013.01); *A61F 2/1635* (2013.01); *B29D 11/023* (2013.01); *A61F 2/1659* (2013.01); *A61F 2002/16965* (2015.04); *B29K 2683/00* (2013.01)

(58) Field of Classification Search
CPC .............................................. A61F 2002/16965
USPC ........................................................ 623/6.6
See application file for complete search history.

(56) References Cited

U.S. PATENT DOCUMENTS

| | | | |
|---|---|---|---|
| 6,450,642 B1 | 9/2002 | Jethmalani et al. | |
| 6,824,266 B2 | 11/2004 | Jethmalani et al. | |
| 6,851,804 B2 | 2/2005 | Jethmalani et al. | |
| 6,905,641 B2 | 6/2005 | Platt et al. | |
| 7,074,840 B2 | 7/2006 | Chang et al. | |
| 7,105,110 B2 | 9/2006 | Platt et al. | |
| 7,210,783 B2 | 5/2007 | Jethmalani et al. | |
| 7,281,795 B2 | 10/2007 | Sandstedt et al. | |
| 7,341,345 B2 | 3/2008 | Azar et al. | |
| 7,837,326 B2 | 11/2010 | Jethmalani et al. | |
| 9,119,710 B2 | 9/2015 | Grubbs et al. | |
| 2006/0261502 A1 | 11/2006 | Platt et al. | |

(Continued)

FOREIGN PATENT DOCUMENTS

WO    WO 2015/022515 A1    2/2015

*Primary Examiner* — David H Willse
*Assistant Examiner* — Javier Blanco

(57) ABSTRACT

A method for adjusting a light adjustable lens in an optical system includes providing a light adjustable lens in an optical system; providing an ultraviolet light source to generate an ultraviolet light; and irradiating the generated ultraviolet light with a light delivery system onto the light adjustable lens with a center wavelength and with a spatial irradiance profile to change a dioptric power of the light adjustable lens by changing a refraction of the light adjustable lens in a refraction-change zone, thereby causing a wavefront sag, defined as half of a product of the change of the dioptric power and the square of a radius of the refraction-change zone, to be within 28% of its maximum over an ultraviolet spectrum.

17 Claims, 12 Drawing Sheets

(56) References Cited

U.S. PATENT DOCUMENTS

| | | |
|---|---|---|
| 2008/0027537 A1 | 1/2008 | Gerlach et al. |
| 2010/0066973 A1 | 3/2010 | Portney |
| 2013/0072591 A1 | 3/2013 | Sandstedt et al. |
| 2016/0324629 A1 | 11/2016 | Sandstedt et al. |

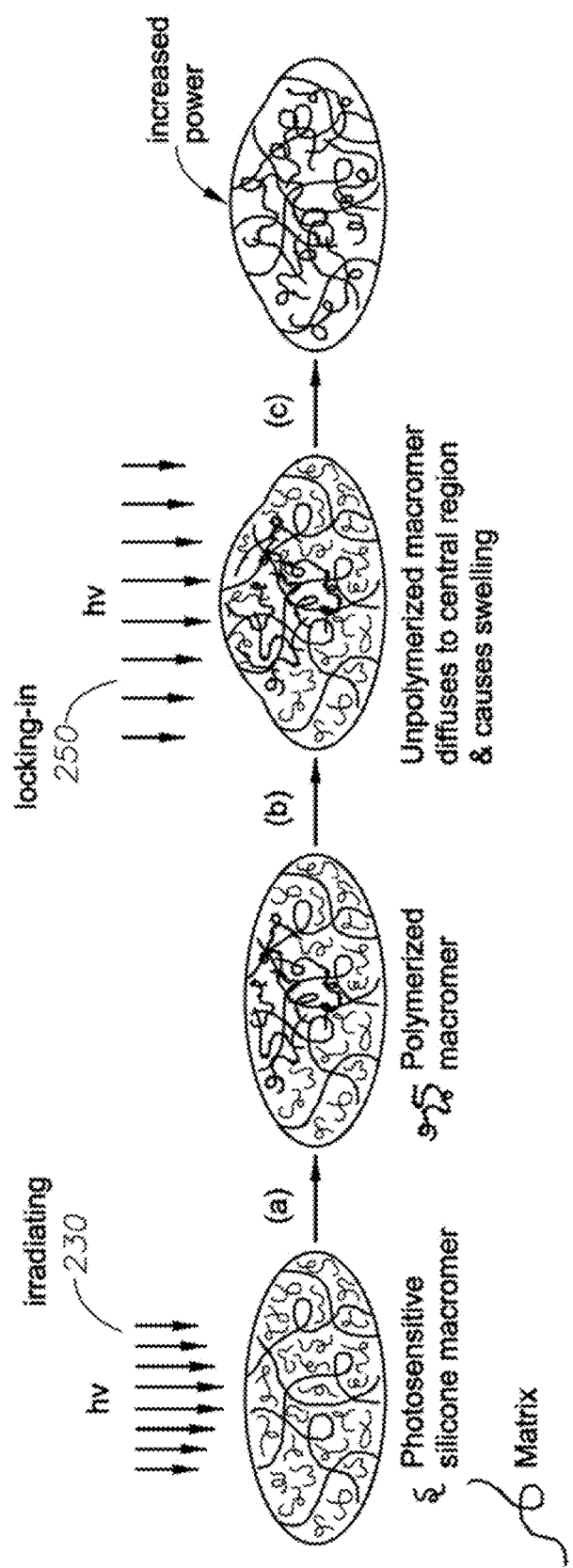

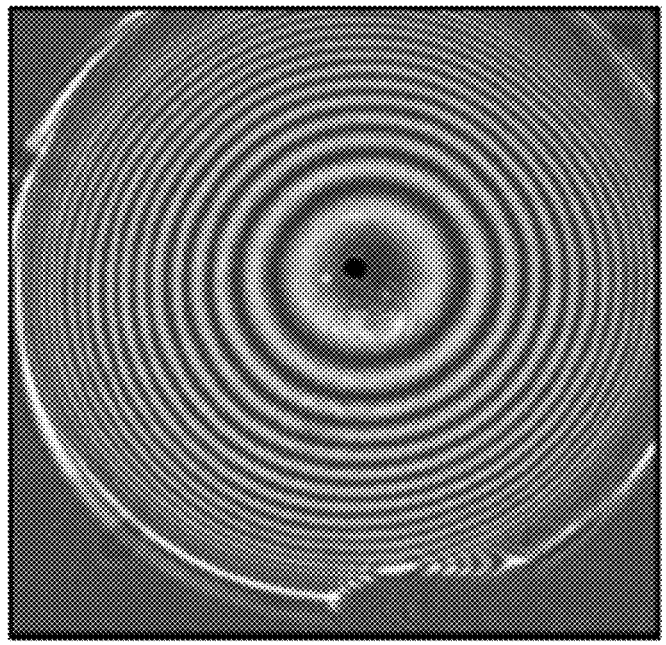
FIG. 8B  λ = 372 nm
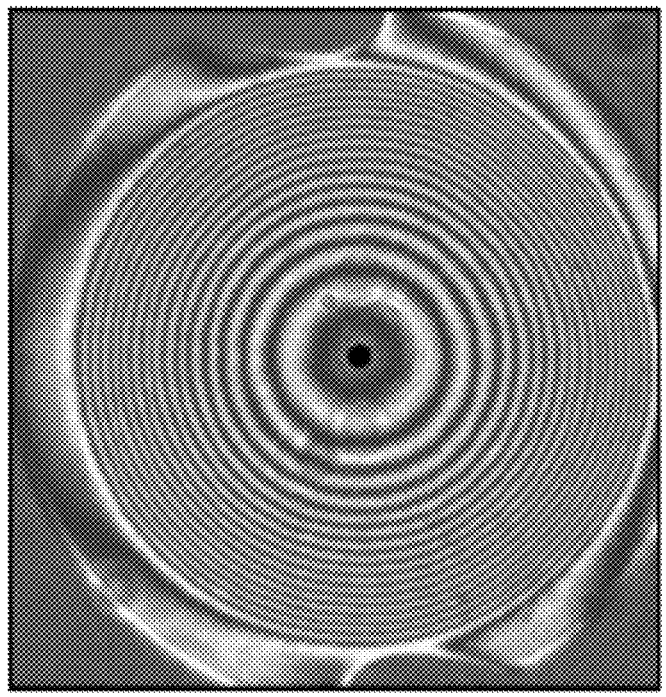
FIG. 8A  λ = 381 nm

METHOD FOR MODIFYING POWER OF LIGHT ADJUSTABLE LENS

CROSS REFERENCE TO RELATED APPLICATION

This patent application is a continuation of, and claims benefit from, co-pending U.S. patent application Ser. No. 15/159,909, entitled "Method for Modifying Power of Light Adjustable Lens," by Robert H. Grubbs and Christian A. Sandstedt, filed on May 20, 2016, hereby incorporated in its entirety by reference, that claims benefit from U.S. Provisional Application No. 62/164,413, filed on May 20, 2015.

TECHNICAL FIELD

This invention relates generally to the post-manufacture alteration of the properties of an optical device, and, more specifically, to modifying the refractive power of light adjustable lenses.

BACKGROUND

A light adjustable lens is an optical device whose refractive properties can be changed after its fabrication and insertion into a human eye. Such lenses are described, for example, in U.S. Pat. Nos. 6,450,642; 6,851,804; 7,074,840; and 7,281,795, the disclosure of all which is incorporated herein by reference. The light adjustable lens (LAL) has a refraction modulating composition dispersed in a polymer matrix. After the lens has been implanted into the eye and refractive stabilization has occurred, deviations from the planned refractive power, and preexisting optical aberrations or those induced by the clinical procedure (e.g. spherical power, astigmatism, spherical aberration), can be measured. In order to correct the optical, or dioptric power, as well as these optical aberrations, the LAL is irradiated, typically with a UV light. This irradiation alters the optical properties of the lens either through changes in its shape, its index of refraction, or both. Following one or several irradiations in which portions of the lens have been exposed to selectively and spatially modify the refractive power, the entire lens is irradiated to "lock in" the modified lens.

The use of UV irradiation has been discussed in the ultraviolet wavelength range of 320-400 nm for post-operatively adjusting the optical power of LALs. For example, a Helium Cadmium (HeCd) laser operating at 325 nm and a mercury (Hg) arc lamp spectrally filtered for the emission lines at 334 and 365 nm have been used for modifying the refractive power of LALs. Additionally, references also mention that tripled frequency laser diode pumped solid state YAG lasers operating at 355 nm, an argon ion laser operating in the 350-360 nm range, a deuterium discharge lamp, and broad-band xenon:mercury lamps operating with any narrow band spectral filter are all useful light sources for conducting UV irradiation on light adjustable materials and lenses.

However, there is still room for improvements related to these sources. When using a coherent source, such as a laser, there is the possibility that the source gets focused to a point on the retina, creating high irradiances that can cause damage. Extended spectrum, incoherent sources such as arc lamps are attractive from the standpoint that they cannot be focused to a tight spot. It is noted though that these sources typically have high output irradiances so their output must be attenuated by as much as a factor of 1/1000 for use in irradiating the light adjustable lenses. Thus, improper use of such incoherent lamps, or a mechanical or electrical failure of the attenuation system could result in inadvertent application of high irradiances to the ocular structures, again resulting in unintended damage. These possibilities, however, can be prevented with a reassuringly strong margin of safety. Therefore, incoherent mercury arc lamps provide a valuable engineering solution for an ultraviolet light source to be used to irradiate LALs implanted into the human eye. Their utility is further underlined by their relatively low cost, and the fact that the filtered 365 nm line from the mercury arc lamp is effective for the photo-polymerization process.

Still, given the high value and demand for achieving optimal clinical outcomes in ophthalmology, as well as the importance of reducing ocular exposure, drive the search for newer generations of lens adjustment systems that can deliver more precise and more predicable clinical outcomes and reduce the ocular exposure even further.

SUMMARY

Embodiments of the invention relate to systems and methods to modify a refractive property of a light adjustable lens by a lens adjustment system that provide improvements in the achieved optical power change and in other optical characteristics, and reduce the dose required for lock-in and the ocular exposure.

Accordingly, embodiments include a method for adjusting a light adjustable lens in an optical system, the method comprising: providing a light adjustable lens in an optical system; providing an ultraviolet light source to generate an ultraviolet light; and irradiating the generated ultraviolet light with a light delivery system onto the light adjustable lens with a center wavelength and with a spatial irradiance profile to change a dioptric power of the light adjustable lens by changing a refraction of the light adjustable lens in a refraction-change zone, thereby causing a wavefront sag, defined as half of a product of the change of the dioptric power and the square of a radius of the refraction-change zone, to be within 10% of its maximum over an ultraviolet spectrum.

Further, embodiments include a lens adjustment system, comprising: an ultraviolet light source to generate an ultraviolet light; and a light delivery system to irradiate the generated ultraviolet light onto a light adjustable lens in an optical system, with a center wavelength and with a spatial irradiance profile to change a dioptric power of the light adjustable lens by changing a refraction of the light adjustable lens in a refraction-change zone, to cause a wavefront sag, defined as half of a product of the change of the dioptric power and the square of a radius of the refraction-change zone, to be within 10% of its maximum over an ultraviolet spectrum.

Further, embodiments include a light adjustable lens comprising: a first polymer matrix; a refraction modulating composition, including a macromer with a photo-polymerizable end group, dispersed in the first polymer matrix; and a photoinitiator; a first ultraviolet absorber with a first absorption coefficient in a first concentration, dispersed in the first polymer matrix; and a back-layer, formed in conjunction with a back surface of the light adjustable lens with a back-layer thickness, the back layer including a second ultraviolet absorber with a second absorption coefficient in a second concentration; wherein the first absorption coefficient, the first concentration, the second absorption coefficient, the second concentration and the back-layer thickness are selected such that a ratio of an irradiance of an ultraviolet light transmitted by the light adjustable lens through the back-layer over an irradiance of the ultraviolet light incident on a front surface of the light adjustable lens is less than 0.1%.

BRIEF DESCRIPTION OF THE DRAWINGS

FIG. 4A is a top/frontal view, and FIG. 4B is a cross-sectional view of the lens, with a posterior UV absorbing back-layer.

FIGS. 5A-D are a schematic representation of the processes and stages of a Hyperopic Power Adjustment Mechanism.

FIGS. 8A-B illustrate interference fringe patterns, indicating the spatial extent of the refraction-change zone 160, formed by the irradiating step 230.

FIG. 10A shows the spectral irradiances incident on the anterior surface of the lens, with integrated irradiances under each curve being approximately the same. FIG. 10B shows the corresponding transmitted spectral irradiances for each of the four center wavelengths.

DETAILED DESCRIPTION

As the Background section described, existing light adjustable lens systems offer good optical performance and are safe. Nevertheless, given the central importance of the quality of the clinical outcomes for patients, it is highly valuable to further increase the optical performance of lens adjustment systems, as well as to further reduce ocular exposure involved.

Figure 1:
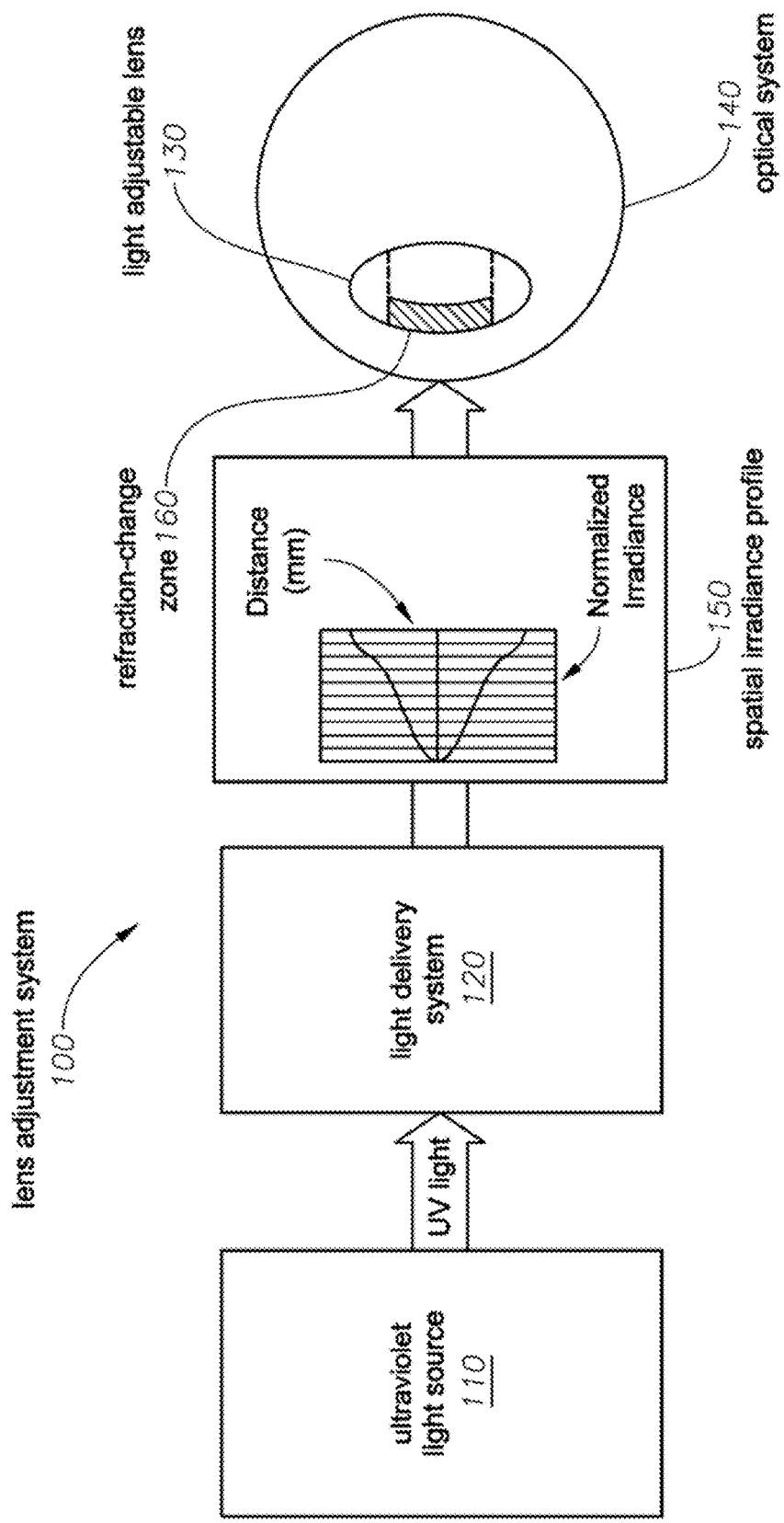
FIG. 1 illustrates an embodiment of a lens adjustment system 100.

In this context, the present document describes new lens adjustment systems and methods that improve the eventual optical performance of the light-adjusted lens, as well as beneficially reduce an ocular exposure associated with the adjustment process. To place the advantages of the lens adjustment systems and methods in context, FIG. 1 illustrates embodiments of a lens adjustment system 100. The lens adjustment system 100 can include an ultraviolet light source 110 to generate an ultraviolet light, a light delivery system 120 to deliver and irradiate the generated ultraviolet light from the ultraviolet light source 110 onto a light adjustable lens 130 in an optical system 140 with a center wavelength and with a spatial irradiance profile 150 to change a dioptric power of the light adjustable lens 130 by changing a refraction of the light adjustable lens 130 in a refraction-change zone 160. The irradiance profile 150 in FIG. 1 is shown with higher resolution in FIG. 7A.

In ophthalmic embodiments of the lens adjustment system 100, the optical system 140 can be a human eye and the light adjustable lens 130 can be a light adjustable intra ocular lens (IOL), implanted into the human eye. In some typical systems, the ultraviolet light source 110 and the light delivery system 120 can irradiate the implanted light adjustable lens 130 to change its dioptric or refractive power to adjust or correct a myopic power, a hyperopic power, astigmatism, a spherical aberration, or a higher order aberration of the human eye in the refraction-change zone 160. This zone 160 can extend partially along an optical axis of the eye, as shown, or in some embodiments, it can extend across the entire depth along the optical axis.

Some of the advantages of the here-described embodiments of the lens adjustment system 100 include the followings. (a) Embodiments increase the achievable maximum dioptric change of the light adjustable lens comfortably above 2 diopters, or 2D using the same irradiances as existing systems. Put differently, the irradiance of the ultraviolet (UV) light needed to achieve the same dioptric changes with the new systems as with existing systems is substantially reduced. Since in more than 95% of cataract surgeries the eventual clinical outcome is within 2D of the targeted dioptric power, the here-described improved systems consolidate the status of the light adjustable lenses as clinical solutions that are capable of delivering the targeted optical outcome in essentially all cataract surgeries.

(b) Further, the here-described systems increase the area of the refraction-change zone 160 of the light adjustable lens 130 to prevent unwanted optical disturbances arising from a boundary with a peripheral refraction-unchanged area of the lens slipping into the visual axis with a large margin. This is another substantial step forward in the optical performance, as the boundary between the refraction-change zone 160 and the refraction-unchanged regions of the light adjustable lens 130 can introduce noticeable distortions. Therefore, it is very valuable to make sure that this boundary region is kept well away from the optical aperture of the eye to solidify the high quality optical performance of the LAL 130. Accordingly, improvements that further expand the radius of the refraction-change zone 160 genuinely enhance the optical performance of the light adjustable lens 130. Classes of additional competing optical performance factors will be described in relation to embodiments below.

It was discovered that it was entirely not obvious how to achieve and improve the above listed optical performance factors (a)-(b) of the lens adjustment system 100. At least the following analysis and development steps had to be performed in the design process.

(1) First, there were a large number of optical performance factors that impacted the optical performance of the lens adjustment system 100 and the light adjustable lens 130 to some degree. It was far from clear a priori which were the high value optical performance factors and which had lesser impact on the overall optical performance. Therefore, identifying the lens dioptric change and the radius of the refraction-change zone 160 as the key optical performance factors to maximize the overall optical performance of the light adjustable lens 130 was a substantive step.

(2) Next, it had to be figured out which system factors can impact most effectively the identified optical performance factors (a)-(b). It has been determined that, of the large number of candidate system factors, specifically the wavelength of the ultraviolet light is one of the system factors that can impact both optical performance factors efficiently.

(3) It was next discovered that the two optical performance factors (a) and (b) favor opposite trends with the wavelength, one grew with increasing wavelength, the other with decreasing wavelength. Therefore, it had to be discovered how to improve both these factors (a) and (b) simultaneously. It has been decided that a properly selected figure of merit is a best way for simultaneously improving both optical performance factors. Moreover, since the wavelength is a continuous variable, the process of simultaneously improving the performance factors with the help of a figure of merit, was selecting the most suitable wavelength values out of an infinite number of possible wavelength values.

(4) It has been decided that a product of the square of the refraction-change zone and the diopter change of the lens, often referred to as a "wavefront sag", or "sag" for short, is a suitable figure of merit for the optical performance maximization out of the large number of possible figures of merit.

(5) Detailed experimentation was needed to determine the wavelength that maximizes the selected figure of merit, from the very large number of possible wavelength values (in principle infinite number of possible values, as discussed before.)

(6) An ultraviolet light source 110 needed to be developed that is capable of delivering the UV light with the performance-maximizing wavelength.

(7) The light delivery system 120 needed to be formed so that it should be capable to impart a suitable spatial irradiance profile 150 on the generated UV light, received from the UV light source 110, to control the radius of the refraction-change zone 160.

(8) The light adjustable lens 130 needed to be formed to be consistent with the selected system factors, e.g. by including a UV light absorber that is sufficiently absorbing at the performance-maximizing wavelength.

Combinations and the eventual effect of the development steps (1)-(8) are well-captured by the description that in embodiments the ultraviolet light source 110 and the light delivery system 120 are configured to irradiate the ultraviolet light onto the light adjustable lens 130 to cause a wavefront sag of the optical system, defined as half of a product of the change of the dioptric power of the optical system and the square of a radius of the refraction-change zone of the light adjustable lens, to be within 10% of its maximum over an ultraviolet spectrum. An explanation of why the wavefront sag was chosen as a compelling figure of merit to balance the competing optical performance factors and system factors is presented later in detail.

In some embodiments, the sag can be within 5% of its maximum over the applied ultraviolet spectrum. Here the ultraviolet spectrum can include the UV-A range, it can include the range of 320 nm-400 nm, or it can include another range in the overall UV region, such as a range of 350 nm-400 nm, or a range of 365 nm-382 nm.

Embodiments of the lens adjustment system 100 with the above identified configurations, exhibiting a near-maximal wavefront sag, are capable of delivering both a dioptric power change in the entire clinically high value range of (−2D, +2D), as well as comfortably make sure that the edge of the refraction-change zone 160 is outside an operational aperture of the optical system 140, such as the human eye. Embodiments of the lens adjustment system 100 that improve both of these optical performance factors in the described, substantial manner, provide a critical, distinguishing characteristic in their overall optical performance and utility over existing systems.

Further, embodiments of the lens adjustment system 100 also reduce the exposure of the retina in cases when the optical system 140 is a human eye. As demonstrated below, the development again included numerous steps again, such as (9) identifying key exposure factors out of the large number of possible performance factors, followed by (10) identifying what system factors can improve the exposure factors in the most efficient manner, then (11) determining the system factors that improve the exposure factors the most out of the continuum, and therefore infinite number of, possible system factors, (12) followed by developing the chemistry and material science of the light adjustable lens 130 to exhibit these optimal system factors. A combination of these development steps (9)-(12) can again critically improve the overall exposure parameters. As demonstrated later, the overall effect can be as high as a factor of 10-20 reduction of the irradiance reaching the retina. Since any substantial improvement of a ocular exposure signals valuable progress, discovering systems and methods via the development process (9)-(12) to reduce ocular exposure by a factor of 10-20 is a critical improvement by any measure. Here, the term "ocular exposure" is used in an inclusive manner: it can include a retinal exposure, a corneal exposure, or an exposure of any ocular tissue.

Finally, in some embodiments, some combination of the development steps (1)-(8) and (9)-(12) can be used to drive the system improvement. For example, the fact that the light source 110 and the light delivery system 120 at the selected wavelength can induce a diopter change of the light adjustable lens 130 more efficiently than in existing systems not only improves the optical performance, but also allows the reduction of the ocular exposure to reach the same diopter change as with previous methods. Thus, improving the system by discovering the most efficient combination of the systems factors based on development steps (1)-(8) and (9)-(12) can be viewed as improving both optical performance and ocular exposure.

Finally, for completeness it is noted that substantial improvements can be achieved already if one or more steps are omitted, or carried out partially, e.g. by enhancing but not optimizing a performance or an exposure factor.

Detailed description of the performance and exposure factors, and the corresponding system factors that improve them critically are described in the remainder of this application.

Figure 2:
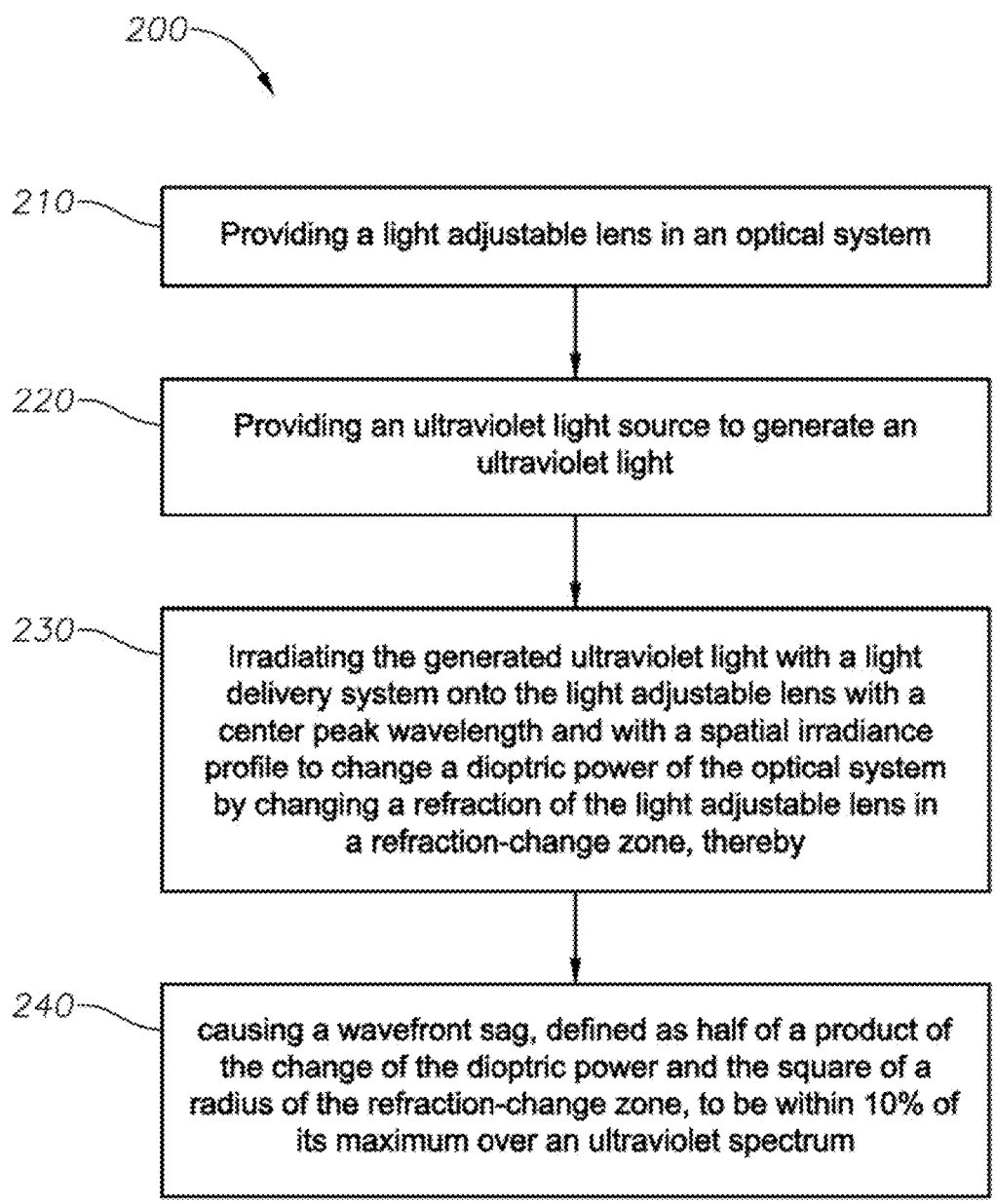
FIG. 2 illustrates a method 200 for adjusting a light adjustable lens 130 in an optical system 140.

FIG. 2 illustrates embodiments of a method 200 for adjusting the light adjustable lens 130 in the optical system 140 using the lens adjustment system 100 that has been discovered by some combination of development steps (1)-(8), possibly further combined with steps (9)-(12).

The method 200 can include:

providing 210 a light adjustable lens 130 in an optical system 140;

providing 220 an ultraviolet light source 110 to generate an ultraviolet light; and irradiating 230 the generated ultraviolet light with a light delivery system 120 onto the light adjustable lens 130 with a center wavelength and with a spatial irradiance profile 150 to change a dioptric power of the optical system 140 by changing a refraction of the light adjustable lens 130 in a refraction-change zone 160, thereby causing a wavefront sag, defined as half of a product of the change of the dioptric power of the optical system 140 and the square of a radius of the refraction-change zone of the light adjustable lens, to be within 10% of its maximum over an ultraviolet spectrum. In some embodiments, the wavefront sag can be within 5% of its maximum over the ultraviolet spectrum. In some embodiments, the irradiating step 230 is referred to as the refractive adjustment step 230.

Figure 3:
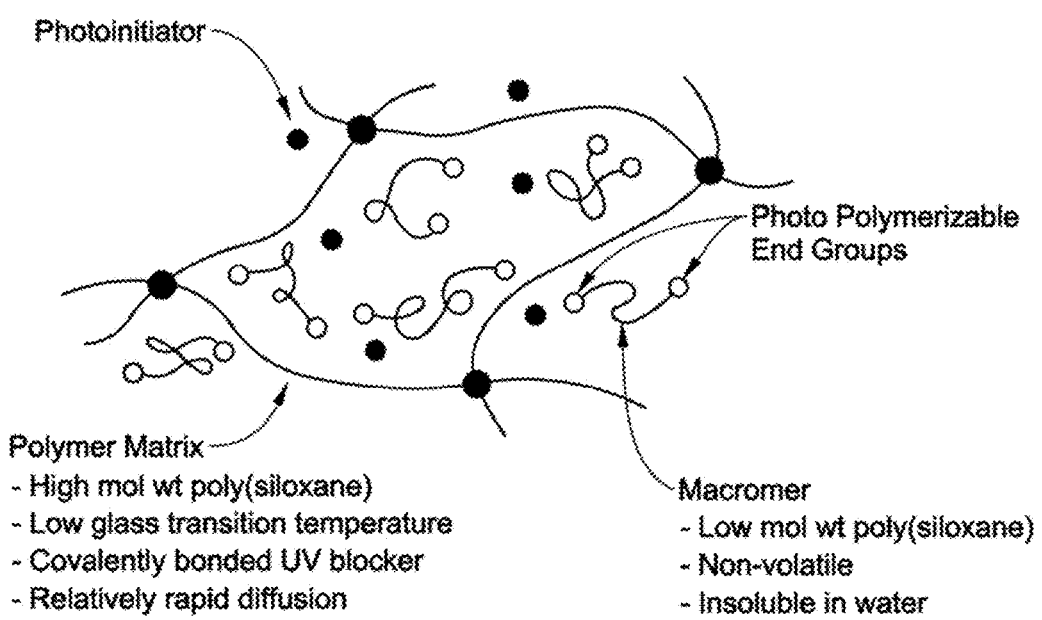
FIG. 3 is a schematic representation of the major light adjustable lens chemical components.

FIG. 3 illustrates that the material and optical design of the light adjustable lens (LAL) is based upon the principles of photochemistry and diffusion, whereby photoreactive components incorporated in a cross-linked silicone lens, or first polymer-matrix, are photo-polymerized upon exposure to UV light of a select spatial irradiance profile. Generally, a LAL comprises a first polymer matrix and a refraction modulating composition dispersed therein. The first polymer matrix forms the optical element framework and is generally responsible for many of its material properties. The refraction modulating composition may be a single compound or a combination of compounds that is capable of stimulus-induced polymerization, preferably photo-polymerization. As used herein, the term "polymerization" refers to a reaction wherein at least one of the components of the refraction modulating composition reacts to form at least one covalent or physical bond with either a like component or with a different component. The identities of the first polymer matrix and the refraction modulating compositions will depend on the end use of the optical element. However, as a general rule, the first polymer matrix and the refraction modulating composition are selected such that the components that comprise the refraction modulating composition are capable of diffusion within the first polymer matrix. Put another way, a loose first polymer matrix can be paired with larger refraction modulating composition components and a tight first polymer matrix can be paired with smaller refraction modulating composition components.

In some specific embodiments, the LAL can be based on the inclusion of photoreactive silicone macromer and photoinitiator within a silicone polymer matrix. Post-operative, in-silt irradiation of the implanted LAL, using targeted dosages of UV light, produces modifications in the lens curvature, thus resulting in predictable changes in the dioptric or refractive power, and in various aberrations, including spherical, cylindrical, and aspheric types.

FIG. 3 is a schematic representation of the LAL and its major constituents. The first component of note is shown as the long connected strands and corresponds to the polymer matrix, which acts to give the LAL its basic optical and mechanical properties. Generally, the polymer matrix is composed of a high molecular weight (>200 k) polysiloxane that also possesses a covalently bonded UV blocker (not shown). Due to its cross-link density and inherent low glass transition temperature (~-125° C.), the LAL's polymer matrix allows for relatively rapid diffusion throughout its polymer network. The second major constituents are the smaller strands with circular endgroups noted as macromer. The macromer is a low, relative to the matrix polymer, molecular weight polysiloxane. From a chemical standpoint, the majority of the macromer chain can be the same as that of the polymer matrix, which allows for essentially infinite miscibility of the macromer within the polymer matrix. The macromer and polymer matrix generally are miscible with each other, thus avoiding the potential for phase separation and subsequent light scatter. A unique aspect of the macromer molecule is the presence of symmetric, photo-polymerizable methacrylate end groups at the end of each macromer chain. In FIG. 3, these photo-polymerizable endgroups are represented by circles at the end of each macromer chain. The final chemical moiety of note is listed as photoinitiators, which act to catalyze the photo-polymerization reaction of the macromer end groups.

Generally, embodiments of the LAL can also comprise a UV absorber in the bulk of the lens in a concentration in the range of 0.0 wt % to 0.05 wt %. The concentration of this UV absorber can be selected by corresponding development steps.

Examples of existing LALs are described, for example, in U.S. Pat. Nos. 6,450,642; 6,851,804; 7,074,840; and 7,281,795, contents of all of which are herein incorporated in their entirety by reference. Several different versions of LAL have been developed by the applicants and are known in the art.

Figure 4A:
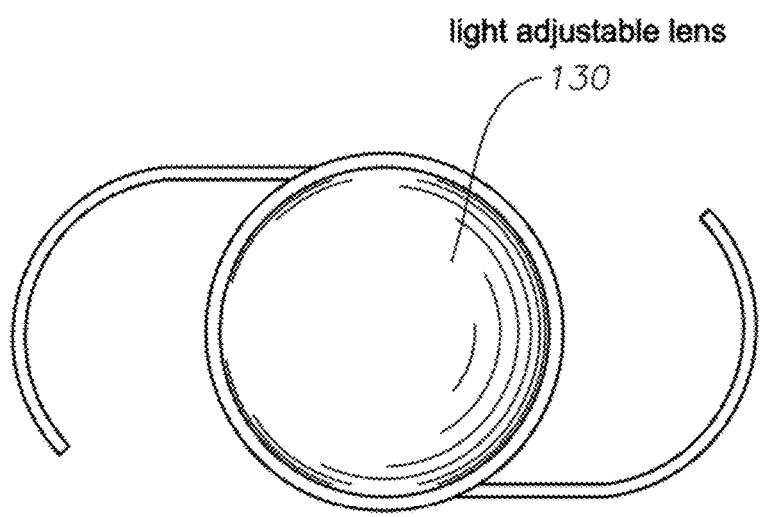
FIGS. 4A-B show embodiments of an existing class of light adjustable lenses.
Figure 4B:
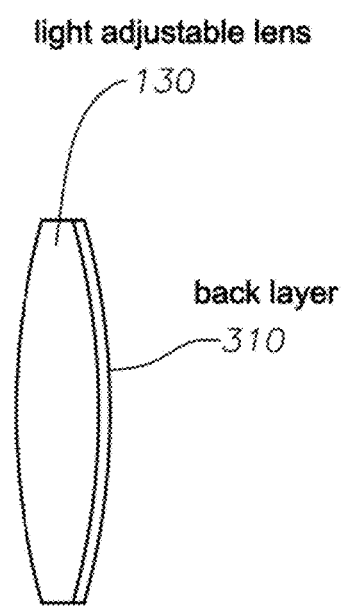

FIGS. 4A-B illustrate a class of existing embodiments of the LAL 130. In some of these embodiments, the LAL can be a foldable, posterior chamber, UV absorbing, three-piece photoreactive silicone lens. Embodiments of the LAL may include blue PMMA (poly methyl methacrylate) modified-C haptics, a biconvex optic having a diameter in the 5 mm-7 mm range, such as 6 mm. Some embodiments can have a squared posterior edge, and an overall length of 10-13 mm. The wt % of the UV absorber in the bulk of the LAL can be 0.04 wt % or higher. The LAL optic design can incorporate a silicone posterior surface layer, or back-layer 310. The thickness of this back-layer 310 can be about 100 μm all across a back surface, or posterior surface of the light adjustable lens 130. In other embodiments, the thickness can be between 50 μm and 100 μm in the center, and can increase gradually to 100 μm at the edge of the light adjustable lens 130. This back-layer 310 can include a higher concentration of a UV absorber than the photoreactive bulk lens material to further enhance the UV absorbing properties of the LAL and provide additional attenuation to reduce ocular exposure during the lens power adjustment and lock-in procedures.

FIGS. 5A-D illustrate that the optical system 140 where the LAL 130 is positioned can be a human eye and the LAL 130 can be a light adjustable IOL. As mentioned before, in a large fraction of cataract surgeries, 95% according to some reports, the clinical outcome for the dioptric power of the eye deviates from the targeted dioptric power by an amount in the (−2D, +2D) range. The here-described lens adjustment systems 100 make it possible to irradiate the LAL 130 to correct this deviation of the patient's vision after the implantation, so that the patient does not have to wear eyeglasses after surgery. In accordance with embodiments of the present invention, following implantation and waiting the necessary time (often 1 to 4 weeks) for refractive stabilization to occur, the deviations from the targeted dioptric outcomes and the aberrations in the eye can be measured. Then the intensity, the spatial irradiance pattern 150, and the duration of the irradiation can be precisely planned to reduce or eliminate the deviations in the dioptric outcomes and for one or more aberrations. Finally, the light source 110 and the light delivery system 120 can be activated to irradiate the light adjustable lens 130 with the planned intensity, profile and duration.

It is mentioned that other uses of the method 200 also exist. For example, embodiments of the method 200 can be used as an aberration conjugator to correct other types of optical systems, including microscopes, telescopes, camera lenses, ex-vivo, custom ordered intraocular lenses (IOLs), before implantation, and custom ordered contact lenses.

Upon exposure to an appropriate energy source, for example, the UV light source 110, the refraction modulating composition, more precisely the photosensitive photo-polymerizable (silicon) macromers of the refraction modulating composition, typically form a second polymer matrix, an interpenetrating network, in the exposed region of the LAL 130, induced by the photo-polymerization by the UV light, as shown in process (a).

FIG. 5B illustrates that this process generates an enhanced density of polymerized, and therefore low mobility macromers in the exposed region, thus reducing the concentration of the more mobile, unpolymerized macromers in the exposed region. This creates a concentration gradient of the mobile macromers, with a corresponding spatial variation of their chemical potential.

In process (b), the more mobile, unpolymerized macromers diffuse or migrate to the exposed region driven by their concentration gradient, and cause a change in the radius of curvature of the light adjustable lens 130. FIGS. 5A and 5C illustrate the case of a hyperopic treatment, when a central region of the LAL 130 was exposed. In other, myopic embodiments, the exposed region is peripheral, depending on whether a hyperopia or a myopia of the eye is being corrected. FIG. 5C illustrates that the macromere diffusion changes the radius of curvature of the surface of the light adjustable lens, thus changing its refractive and dioptric power.

The amount of refraction modulating composition that migrates into the exposed region is time dependent and may be precisely controlled during the irradiating step 230. After long enough time, the unpolymerized macromers of the refraction modulating composition re-equilibrate, and the diffusion comes to a halt. Generally, the equilibrium is re-established in 24-48 hours post irradiation. The just-described process of the irradiating step 230, followed by an appropriate time interval to allow for macromer diffusion, may be repeated until the exposed region of the optical element has reached the desired optical property, e.g., the targeted change of optical power, dioptric power, aberration, refractive index, or shape.

Further, FIG. 5C illustrates that when the targeted enhanced central curvature is reached, caused by the diffusion of the mobile macromers, the method 200 can include a subsequent, "locking-in irradiation" 250 to solidify the successfully reached targeted optical power change by immobilizing all macromers that remained mobile after the irradiating steps 230. This locking-in irradiation 250 can be applied not only to a selected region of the LAL 130, but to a broad region, or large fraction of the LAL 130, to photo-polymerize all remaining and still mobile macromers that were unpolymerized by the previous, spatially selective and lower intensity irradiating step 230. Without this locking in 250, mobile macromers would remain in the LAL 130, and they could move around, causing further, unplanned dioptric power changes when exposed to further external stimuli, such as the patient looking, even accidentally, into the Sun.

FIG. 5D illustrates a typical end point of the method 200, wherein the vast majority, or essentially all of the macromers got polymerized, either in process (a), having increased a dioptric power of the LAL 130 by a targeted amount, or in process (c), having "locked in" the achieved enhanced curvature and thus the increased dioptric power of the swollen region of the LAL 130 by polymerizing the remaining mobile macromers.

As an example, if the central portion of the lens is irradiated and the peripheral portion is left non-irradiated, unreacted macromers diffuse into the center portion causing an increase in the lens power (FIG. 5B). Conversely, by irradiating the outer periphery of the lens, macromer migrates outward causing a decrease in the lens power. Cylindrical power adjustments can be achieved in a similar manner by removing power in one meridian while adding power in the perpendicular meridian. By using a digitally generated beam profile, in other words, the spectral irradiance profile 150, the axis of the cylindrical correction can be precisely aligned by digitally rotating the spatial irradiance profile. By controlling the radiant exposure (i.e. beam irradiance and duration), spatial irradiance profile 150 and target area, physical changes in the radius of curvature of the lens surface are achieved, thus modifying the refractive power of an implanted light adjustable lens to add or subtract spherical power, remove toricity, or adjust the amount of asphericity. Once the appropriate power adjustment and/or visual outcomes are achieved, the entire lens is irradiated in the locking-in step 250 to polymerize the remaining unreacted macromer to prevent any additional change in lens power. By irradiating the entire lens, further macromer diffusion is prevented thus no additional change in lens power results.

Having reviewed the photo-chemistry of changing the optical and dioptric power of the light adjustable lens 130, the following development questions emerge: (1) which optical performance factors are the most critical for the overall performance of the light adjustable lens, (2) which system factors impact these performance factor in the most efficient and critical manner. Several answers to these questions are discussed in the next sections.

Optical Performance Improvement 1

As discussed above, one of the highest value optical performance factors for the clinical utility of the lens adjustment system 100 for cataract surgeries is to reliably deliver a dioptric change across the entire (−2D, +2D) range, since more than 95% of cataract surgeries today end up with clinical outcomes that differ from the planned or targeted optical power by up to 2 diopters. This is the optical performance factor which is first investigated. Here it is noted that the dioptric power change can be that of the light adjustable lens 130, or that of the entire optical system 140 that includes the LAL 130. In the case when the optical system 140 is the human eye, it includes further optical elements, such as the cornea which impact how the optical power change of the LAL 130 translates into the optical power change of the entire optical system of the eye 140.

Figure 6:
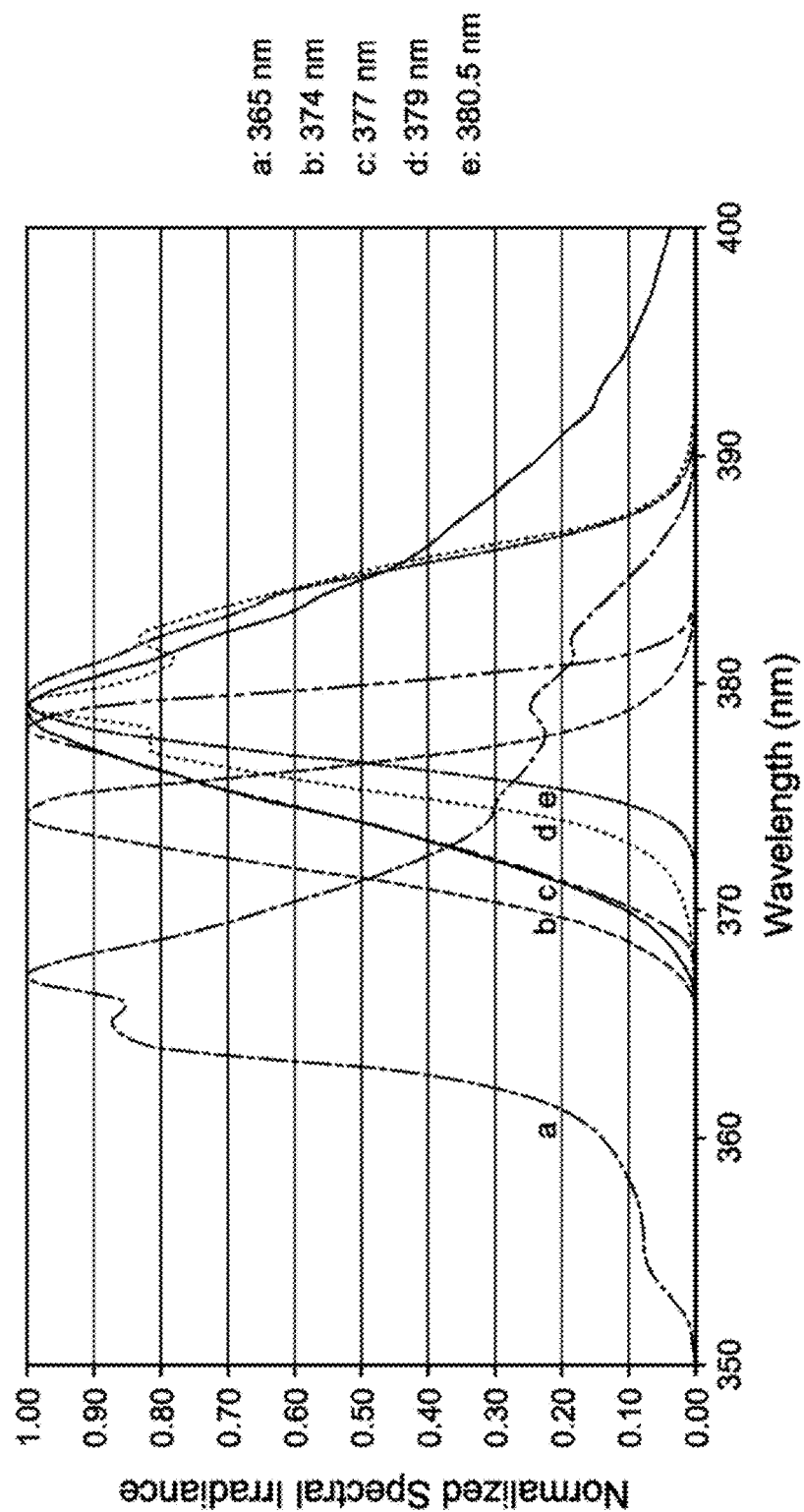
FIG. 6 shows the normalized spectra of ultraviolet light sources with different center wavelengths, used to analyze embodiments of the existing light adjustable lenses.

A series of experiments were conducted to determine what system factors impact the performance factor of dioptric change the most critically. First, the dependence of the optical performance factor on the wavelength of the applied UV light source 110 was examined. While early lens adjustment systems were confined to mercury arc lamps as light sources that emit at 365 nm, recent years have seen a dramatic upsurge in the development of high power output, near UV LED light sources that are produced with discrete spectral outputs from 365 nm to 405 nm. FIG. 6 displays the normalized spectral output of a UV LED (solid black curve, (c)) with a center wavelength at 379 nm. This spectrum is visibly very broad, with a large full width half maximum (FWHM), larger than 10 nm. To determine the wavelength dependence more precisely, commercially available band-pass interference filters were inserted into the beam path of this UV LED source. These discrete spectral bandpass filters were centered at different center wavelengths with significantly narrower FWHM, typically in the range of 6-8 nm. To this end, different bandpass filters with central pass wavelengths of 370 nm, 375 nm, and 380 nm, were inserted into the beam path of the 379 nm LED and produced the spectral curves plotted in FIG. 6. For comparison, the spectral output of the 365 nm from the mercury arc lamp (dashed black line, (a)) is also shown. Table 1 summarizes the spectral characteristics of the 5 curves.

TABLE 1

Summary of the spectral characteristics of a 365 nm filtered mercury arc lamp, a commercially available UV LED light source, and the UV LED source with a 370 nm bandpass, 375 nm bandpass, and 380 nm bandpass filter inserted into its beam path.

| Spectral Bandpass | Center wavelength (nm) | FWHM (nm) |
|---|---|---|
| Hg Arc + 365 nm BP filter | 365 | 9 |
| 379 LED | 379 | 10 |
| 379 LED + 370 nm BP | 374 | 6 |

TABLE 1-continued

Summary of the spectral characteristics of a 365 nm filtered mercury arc lamp, a commercially available UV LED light source, and the UV LED source with a 370 nm bandpass, 375 nm bandpass, and 380 nm bandpass filter inserted into its beam path.

| Spectral Bandpass | Center wavelength (nm) | FWHM (nm) |
|---|---|---|
| 379 LED + 375 nm BP | 377 | 6 |
| 379 LED + 380 nm BP | 380.5 | 8 |

Figure 7A:
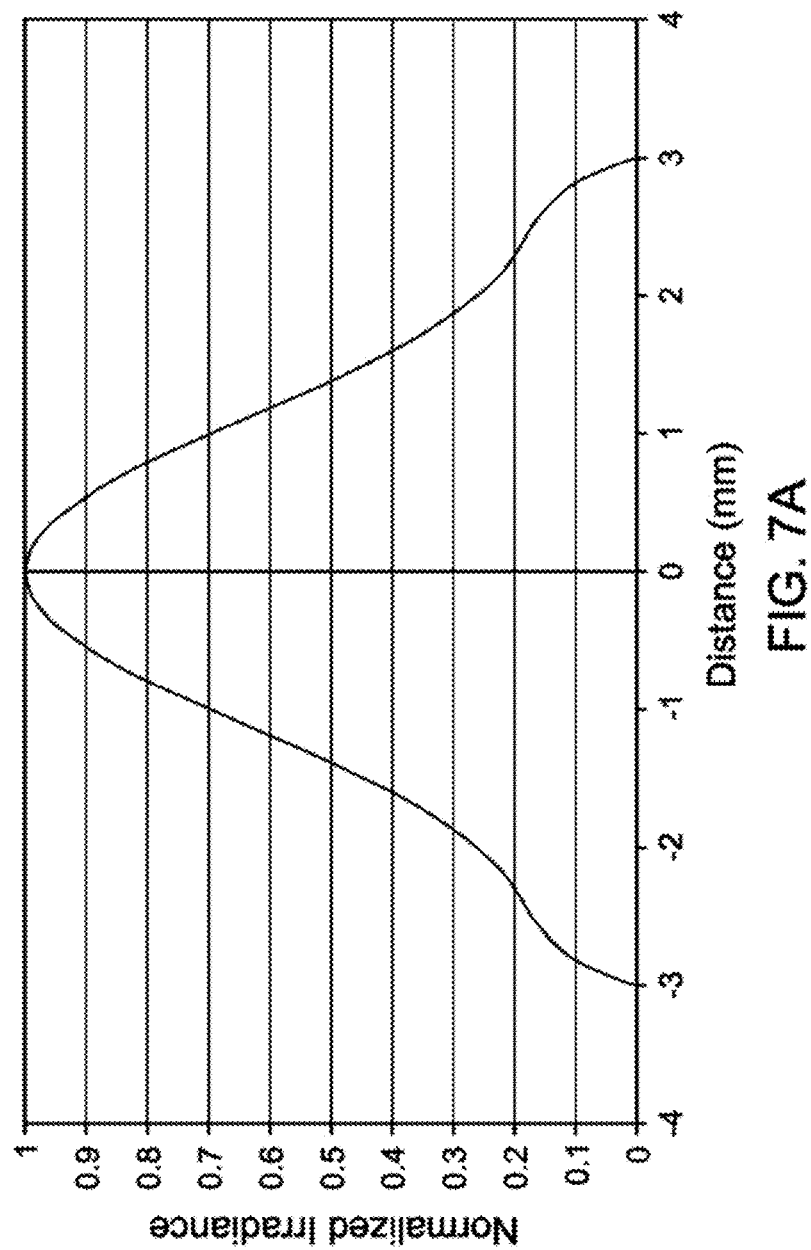
FIGS. 7A-B show spatial irradiance profiles to adjust hyperopic and myopic optical systems.
Figure 7B:
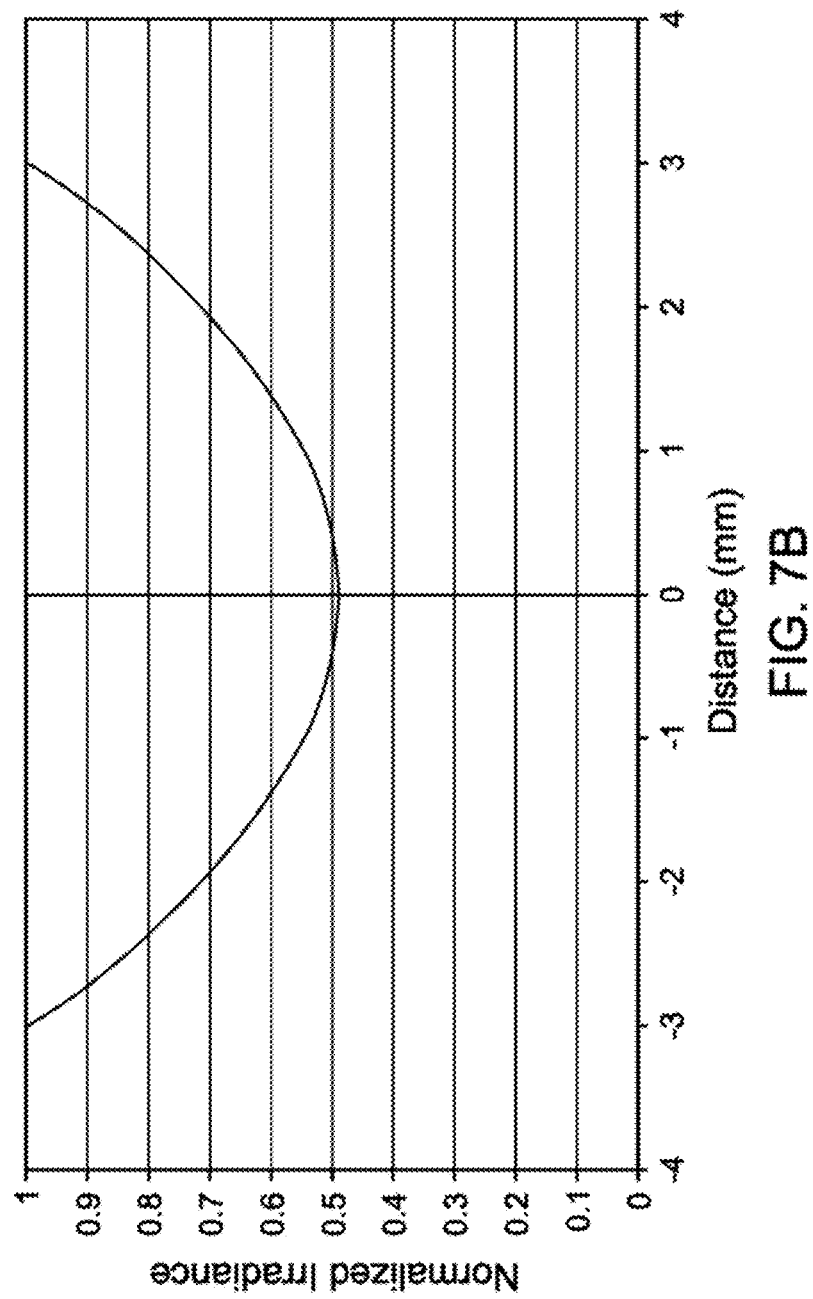

FIGS. 7A-B illustrate that to investigate the potential improvement in power change due to tuning of the applied wavelength, a series of light adjustable lenses were irradiated with the same spatial irradiance profile 150, the same average irradiance, and the same treatment duration, but the spectral band of the irradiating beam was changed. Four different spectral bandpasses were applied and correspond to the mercury arc lamp+the 365 nm BP filter, the 379 nm UV LED+the 370 nm BP filter, the 379 nm UV LED+the 375 nm BP filter, and the 379 nm UV LED+the 380 nm BP filter. FIG. 7A illustrates a spatial irradiance profile used for a hyperopic adjustment with a targeted power change of +1.25 D. FIG. 7B illustrates a spatial irradiance profile used for a myopic adjustment with a targeted power change of −0.75 D. Four individual light adjustable lenses were irradiated with identical treatment conditions and spectral bandpasses.

Table 2 summarizes the refractive power changes, referenced to the spectacle plane of the optical system. In embodiments, the refractive power change can characterize only the light adjustable lens 130, in others, the entire optical system 140. When the optical system 140 is a human eye, the cornea does impact how the change of the optical power of the lens 130 translates into a change of the optical power of the entire eye. The second row in Table 2 lists the hyperopic and myopic refractive changes for a series of existing LAL embodiments, irradiated with a filtered 365 nm emission line from the mercury arc light source. The next three rows correspond to the adjustment data using spectral bandpasses that possess longer wavelengths. Inspection of the power change data for these three bandpasses, as well as their power change ratios relative to the mercury arc source indicated that by tuning the irradiating wavelength to a spectral region where the relative absorption ratio between the photoinitiator and the UV absorber is larger, it was possible to achieve greater power change for the same nominal exposure conditions.

TABLE 2

Power change of LALs after hyperopic and myopic adjustments as a function of different spectral bands. Each reported power change value is the average of 4 individual LALs that were adjusted with the same nomogram treatment conditions.

| Spectral Bandpass | Hyperopic Adjustment [D] | Hyperopic Power Change Ratio of the Applied Spectral Bandpass Relative to that of the Filtered Hg Arc Source | Myopic Adjustment [D] | Myopic Power Change Ratio of the Applied Spectral Bandpass Relative to that of the Filtered Hg Arc Source |
|---|---|---|---|---|
| 365 nm Hg Arc + Chroma K | 1.25 ± 0.04 (n = 4) | 1.00 | −0.78 ± 0.09 (n = 4) | 1.00 |
| LED Light Source + 370 nm BP | 1.47 ± 0.02 (n = 4) | 1.18 | −0.88 ± 0.05 (n = 4) | 1.13 |
| LED Light Source + 375 nm BP | 1.60 ± 0.03 (n = 4) | 1.28 | −0.94 ± 0.04 (n = 4) | 1.21 |
| LED Light Source + 380 nm BP | 1.85 ± 0.05 (n = 4) | 1.48 | −1.04 ± 0.03 (n = 4) | 1.33 |

Similarly, Table 3 summarizes a series of additional refractive adjustments performed with three of the four spectral bands. For these adjustments, a single nomogram treatment protocol was applied with a single spatial irradiance profile that corrects for both hyperopic and astigmatic refractive errors, and also induces negative $4^{th}$ order spherical aberration for the correction of presbyopia. The second row of the table displays the adjustment results using the filtered mercury arc source. The third and fourth rows summarize the refractive change data after application of spectral bands with longer wavelengths. Comparison of these last two cases indicates, a dramatic increase in power change and induction of $4^{th}$ order spherical aberration even though the applied spectral bandpass was shifted only to slightly longer wavelengths. This disproportionately strong response of the refractive changes even to small adjustments of the light source wavelength is a profound demonstration on the non-triviality of analyzing and exploring the optical performance factors and their dependence on the various system factors as key parts of the development process

TABLE 3

LAL power change as a function of different spectral bands. The applied treatment protocol corrected for both hyperopic and astigmatic refractive errors and induced negative asphericity for the treatment of presbyopia. Each reported power change value is the average of 4 individual LALs that were adjusted with the same nomogram treatment condition.

| Spectral Bandpass | Hyperopic Adjustment [D] | Power Change Ratio of the Applied Spectral Bandpass Relative to that of the Hg Arc Source | Astigmatic Adjustment [D] | Astigmatic Power Change Ratio of the Applied Spectral Bandpass Relative to that of the Hg Arc Source | Δ4th Order Spherical Aberration (μm) | Δ4th Order Spherical Aberration Ratio of the Applied Spectral Bandpass Relative to that of the Hg Arc Source |
|---|---|---|---|---|---|---|
| 365 nm Hg Arc + Chroma K | 0.63 ± 0.02 (n = 4) | 1.00 | −1.04 ± 0.09 (n = 4) | 1.00 | −0.33 ± 0.01 (n = 4) | 1.00 |
| LED Light Source + 375 nm BP | 1.02 ± 0.05 (n = 4) | 1.62 | −1.68 ± 0.07 (n = 4) | 1.62 | −0.44 ± 0.01 (n = 4) | 1.33 |
| LED Light Source + 380 nm BP | 1.30 ± 0.03 (n = 4) | 2.06 | −2.07 ± 0.06 (n = 4) | 1.99 | −0.58 ± 0.02 (n = 4) | 1.76 |

These experiments revealed several key lessons. (a) Varying the wavelength of the light source 110 has a critically strong impact on the optical performance: a 15 nm change of the 365 nm wavelength, a mere 4% relative change, can double the change in the refractive outcome. This makes the wavelength a critical system factor. (b) The longer the wavelength, the bigger the dioptric change: the dioptric change increases with increasing wavelength. It would be compelling to conclude from these results that the UV light source 110 and the light delivery system 120 should be configured to deliver the longest possible wavelength UV light to induce the maximum dioptric change in the LAL 130.

However, for a comprehensive study of the optical performance of the lens adjustment system 100, other optical performance factors were examined as well. FIGS. 8A-B illustrate a study of interference fringes of the light adjustable lenses after the irradiation with a standard Zygo interferometer. The spatial extent of the interference fringes reveals the radius of the refraction-change region 160 whose radius of curvature has been affected by the irradiating step 230.

Remarkably, it has been observed that with all other system factors being equal, such as irradiance profile and irradiance, irradiations with longer wavelengths resulted in smaller radius for the refraction-change zone 160. As mentioned before, maximizing the radius of the refraction-change zone 160 is another high value optical performance factor, since the edge of the refraction-change zone 160 is observed to be quite well-defined and thus may introduce noticeable optical distortions, if it is inside the operational aperture of the optical system 140. In the embodiments when the optical system 140 is the human eye, this optical performance requirement approximately translates into the radius of the refraction-change region 160 needing to be in the 4.5 mmm-6 mm range. In some embodiments, the radius needs to be greater than 5 mm, in others, greater than 5.3 mm.

Based on the above considerations, a study was carried out how to improve the optical performance of the light adjustable lens comprehensively. A "Figure of merit" has been devised to balance the competing design forces of (a) needing to increase the wavelength to increase the dioptric change versus (b) needing to decrease the wavelength to increase the radius of the refraction-change zone.

Figure 9:
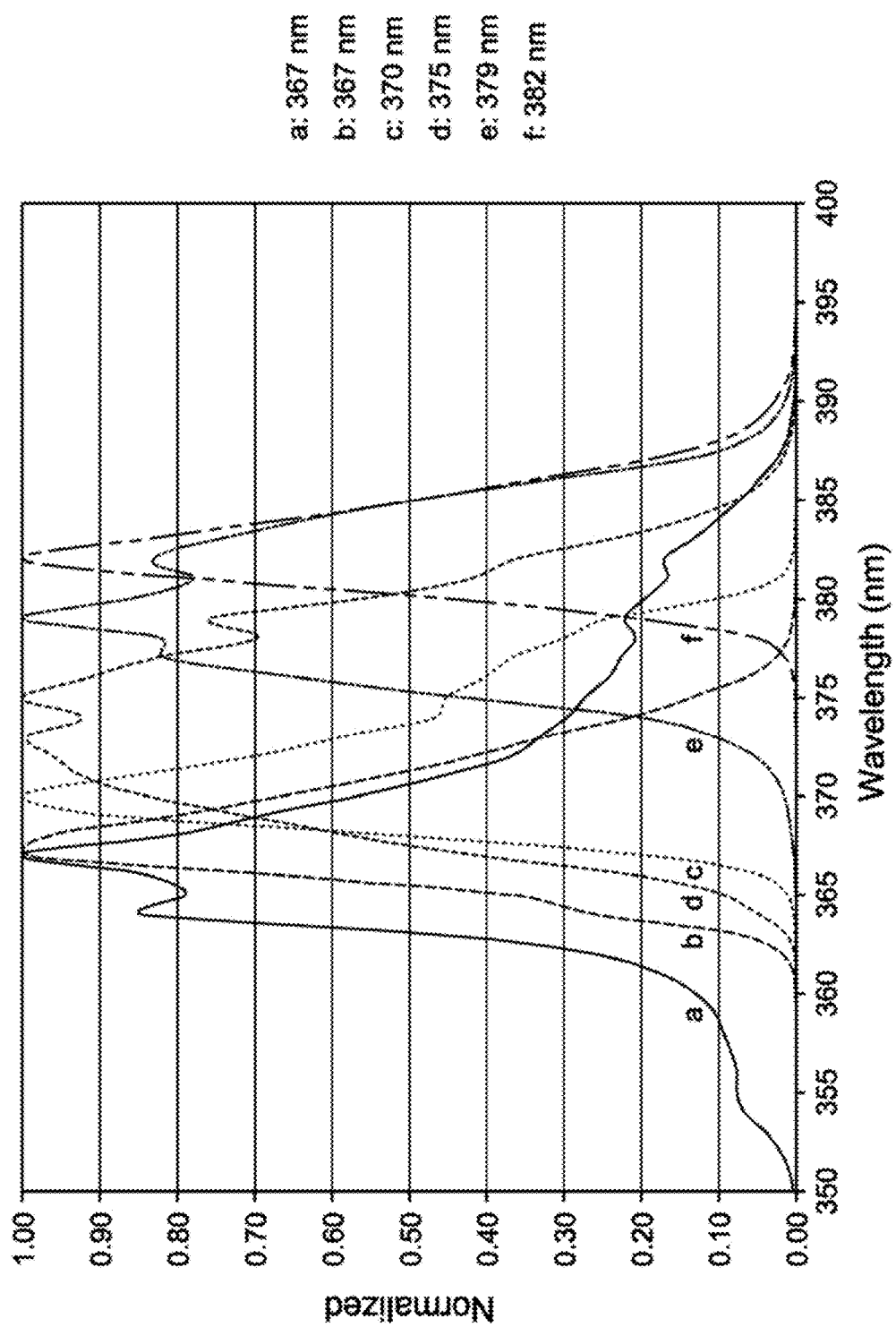
FIG. 9 shows the normalized spectra of six different light sources having different center wavelengths, used to characterize embodiments of a light adjustable lens 130.

FIG. 9 shows a series of normalized spectral bandpasses created by the insertion of different bandpass filters into the beam path of a mercury arc lamp source to produce a series of spectra with center wavelengths ranging from 367 nm to 382 nm. These six spectral bandpasses were then used to irradiate a series of LALs. As a Figure of merit, the induced "wavefront sag" has been selected. The wavefront sag, or "sag" for short, is half of a product of the radius of the refraction-changed zone of the lens squared and the dioptric power change:

$$Sag = \Delta(\text{Dioptric Power}) * y^2 / 2$$

where y is the radius of refraction-change zone of the lens, and Δ(Dioptric Power) is the change in dioptric power from pre-irradiation to post irradiation, measured in units of 1/length, such as 1/microns. This value can describe the dioptric power change of the light adjustable lens 130, or that of the entire optical system 140 that includes the light adjustable lens 130.

The second row in Table 4A provides the refractive change data for the 365 nm filtered mercury arc lamp. Each successive row displays the corresponding data for spectral bandpasses, and thus center wavelengths shifted to longer wavelengths. The sag data is provided in relative terms, as a percent of its maximum value across the investigated UV spectrum. Remarkably, it is noted that the sag data exhibits a maximum as a function of wavelength. This indicates that the selected Figure of merit, the wavefront sag, is useful to determine a compromise wavelength that balances the competing forces of increasing dioptric power change versus increasing the radius of the refraction-change zone. Since the absolute values of the sag depend on secondary details of the light adjustable lenses, the results are presented in relative terms, with 100% indicating the maximum sag, and giving other sag values as a percent of this maximum value.

TABLE 4A

Relative variation of wavefront sag as a function of center wavelength.

| Central Wavelength (nm) | FWHM (nm) | Relative Average Wavefront Sag (%) |
|---|---|---|
| 367 | 9 | 82% (n = 4) |
| 367 | 7 | 87% (n = 4) |
| 370 | 6 | 100% (n = 4) |
| 375 | 14 | 100% (n = 3) |
| 379 | 10 | 97% (n = 4) |
| 382 | 5 | 93% (n = 4) | with a typical error bars of a few percent.

Table 4B illustrates an analogous experiment on another embodiment of the light adjustable lens 130, with some system factors, such as the UV absorber concentration slightly modified.

TABLE 4B

Relative variation of wavefront sag as a function of center wavelength.

| Center wavelength (nm) | FWHM (nm) | Relative Wavefront Sag (%) |
|---|---|---|
| 366.7 | 7.6 | 72% |
| 372 | 1.9 | 86% |
| 374 | 5.7 | 96% |
| 375.5 | 7.2 | 94% |
| 375.6 | 3.7 | 94% |
| 377 | 8.0 | 100% |
| 381.4 | 8.7 | 95% |

Based on these observations, it is concluded that the wavefront sag is a useful figure of merit to determine which values of critical system factors maximize the best optical performance, balancing competing individual design factors. Therefore, in some embodiments of the lens adjustment system, the various system factors are chosen such that the wavefront sag is within 10% of its maximum over an ultraviolet spectrum. In other embodiments, these system factors are chosen so that the wavefront sag is within 5% of its maximum over the same ultraviolet spectrum. These choices identify lens adjustment systems with a favorable overall optical performance.

In some embodiments, these considerations translate to the ultraviolet light source 110 and the light delivery system 120 irradiating the light adjustable lens 130 with the ultraviolet light having a center wavelength in a range of 370 nm to 390 nm. In other embodiments, they irradiate the light adjustable lens 130 with the ultraviolet light having a center wavelength in a range of 374 nm to 382 nm. Finally, in some embodiments, a center wavelength in the regime of 375-377 nm can be used.

Further, since the wavefront sag and other optical performance factors are quite sensitive to the FWHM value of the UV light as well, and get closer to their most preferred behavior for narrower FWHM values, in some embodiments the ultraviolet light source and the light delivery system can be configured to irradiate the light adjustable lens with the ultraviolet light having a full width half maximum (FWHM) spectral bandwidth less than 10 nm. In others, with the ultraviolet light having a full width half maximum spectral bandwidth in a range of 2 nm to 8 nm.

The results were sensitive not only to the center wavelength and to the FWHM values of the light source. It was observed that the spectrum of the mercury arc lamp in fact contained a substantial red-shifted tail, a portion of its spectrum extending all the way to 390 nm. While portions of this irradiance in the 370-380 nm region may be helpful, the irradiance at the higher wavelengths, above 380-385 nm is not optimal. Therefore, the irradiating step 230 of the method 200 in some embodiments can include irradiating the light adjustable lens 130 by ultraviolet light filtered by a bandpass filter in the light delivery system 120, or in the light source 110 itself, which suppresses at least a portion of an undesirable foot of the spectrum. In some embodiments, this bandpass filter can cause an extent of a spectrum of the ultraviolet light source, at e.g. 20% of the spectrum's maximum and at wavelengths longer than the center wavelength, to be less than twice an extent of the spectrum of the ultraviolet light source, at 20% of the spectrum's maximum, at wavelengths shorter than the center wavelength. In short, some embodiments of the light delivery system 120 can be configured to remove at least a portion of the long wavelength, red-shifted tail of the spectrum.

Optical Performance Improvement 2

The above described embodiments delivered high optical performance, determined by analyzing a judiciously chosen Figure of merit, the wavefront sag. In other embodiments, other optical performance factors can be improved as well. For example, the importance of reliably achieving a plus/minus 2 Diopter refractive power change with the lens adjustment system is also a high value optical performance factor. Some of the above-described light adjustable lenses exhibited less dioptric changes. Therefore, further studies of the system factors were carried out to determine ways to deliver the desirable plus/minus 2D dioptric change.

Before proceeding, it is mentioned that the dioptric change can be measured for the entire optical system 140, with the light adjustable lens 130 implanted, or embedded in it. Other optical elements of the optical system may impact this total diopter change. For example, in the case when the optical system is a human eye, it additionally includes a cornea which does impact the optical power and its changes. In this case of the human eye, the dioptric change of plus minus 2 diopters can be measured in, or referenced to, the spectacle plane of the eye. In some embodiments, the dioptric change may refer to that of the lens 130 alone. In some embodiments, a dioptric change of plus minus 3 diopters may be desirable to address exceptional cases.

The studies started with an analysis of the dependence of the absorption properties of the UV absorber materials on wavelength, chemical composition and concentration. As described earlier, the photo-polymerization process of the light adjustable lens is catalyzed by a photoinitiator. The photoinitiator, upon absorption of a photon, decomposes to form active radicals that chemically react with the methacrylate end groups of the macromer to start the polymerization process. Another UV absorbing species in the bulk of the lens is the UV absorber. This molecule also absorbs light in the UV, but does not participate in the photo-polymerization reaction. Instead, this molecule absorbs UV light and dissipates the absorbed energy either as heat or through fluorescence. In some existing lenses, the photo-polymerization of the light adjustable lens is accomplished by using the filtered, 365 nm (FWHM≤10 nm) line from a mercury arc lamp. The dependence of the absorption of the photoinitiator and the UV absorber on the wavelength was studied again using light sources with their center wavelengths sweeping across a UV spectrum.

Table 5 displays the absorption coefficients of the photoinitiator (PI), $BL_4B$, and bulk UV absorber as a function of wavelength between 355 and 390 nm. The last row of Table 5 displays the ratio of the photoinitiator's absorption coefficient relative to that of the UV absorber from 355 nm to 390 nm. Inspection of the ratios between 360 and 370 nm, i.e. across the FWHM spectral band of the 365 nm emission line, indicates a value of only 0.17. From an absorption probability standpoint, this means that for every 100 photons irradiating the lens, 83 are absorbed by the UV absorber and 17 are absorbed by the photoinitiator: only 17 of the photons participate in the photo-polymerization reaction. However, inspection of this ratio from 375 nm to 390 nm indicates that this ratio increases dramatically, making it another critical system factor. Therefore, by tuning the applied wavelength to longer values, the photo-polymerization process should become more efficient.

However, just like in the section "Optical performance improvements 1", a competing system factor was identified once more. It was observed that the absolute absorption of both the photoinitiator and the UV absorber drop off significantly as 385 nm is approached and exceeded. Therefore, ultraviolet light with center wavelengths around and above 385 nm is absorbed with low efficiency and thus both the photoinitiator and the UV absorber rapidly become ineffective above these wavelengths.

Therefore, balancing the ratio of absorption coefficients preferring longer wavelengths while the absolute value of the absorptions disfavoring wavelengths above 380 nm, the wavelength region around 380 nm can be identified as offering the most efficient photo-polymerization process and delivering the best optical performance from the aspect of absorption efficiency.

TABLE 5

Absorption coefficients for the light adjustable lens's bulk UV absorber and photoinitiator ($BL_4B$) from 355 nm to 390 nm.

| Absorbing Species | Absorption Coefficient ($mm^{-1}$) | | | | | | | |
|---|---|---|---|---|---|---|---|---|
| | 355 nm | 360 nm | 365 nm | 370 nm | 375 nm | 380 | 385 | 390 |
| Photoinitiator PI | 0.644 | 0.613 | 0.484 | 0.375 | 0.325 | 0.260 | 0.169 | 0.117 |
| UV Absorber | 3.773 | 3.357 | 2.876 | 2.307 | 1.628 | 0.957 | 0.452 | 0.171 |
| Ratio of PI/UV Abs | 0.17 | 0.18 | 0.17 | 0.16 | 0.20 | 0.27 | 0.37 | 0.69 |

Table 6 shows that this analysis and optimization of competing optical absorption performance factors remarkably delivered the desired improved optical performance: a dioptric change in excess of 2 Diopters essentially at the expected wavelengths of about 380 nm.

TABLE 6

Hyperopic power change at various wavelengths, with a beam diameter approximately 5.3 mm.

| Center wavelength (nm) | Dioptric Power Change (D) |
|---|---|
| 365 | +1.22 ± 0.03 |
| 372 | +1.56 ± 0.05 |
| 374 | +1.76 ± 0.03 |
| 375.5 | +1.80 ± 0.07 |
| 375.6 (narrow fwhm) | +1.69 ± 0.03 |
| 377 | +1.87 ± 0.03 |
| 381.4 | +2.17 ± 0.05 |

This analysis revealed that it is possible to choose a photoinitiator and a UV absorber with such absorption coefficients and in such concentration that they can deliver a plus/minus 2 Diopter refractive change in a wavelength region that was identified based on the figure of merit of maximizing the ratio of absorption coefficients of the photoinitiator over the absorption coefficient of the UV absorber, with the added consideration that an absolute value of these absorption coefficients remained high enough to make the photo-polymerization efficient.

This "Optical performance improvement 2" section described some of the additional examples of the optical performance factors besides the factors (a) and (b) discussed in the opening passages. Just like explained in those passages, these additional optical performance factors were identified out of the many possible factors, a multidimensional design and development space was created, followed by a type of figure of merit being developed to guide a maximalization process. Finally the system factors that impacted these optical performance factors in the most critical manner were identified and tuned to their values that provided the maximal improvement of the optical performance of the lens adjustment system 100, all in analogy with the steps (1)-(12) described in the opening passages.

Optical Performance Improvement 3

The sections "Optical performance improvements 1" and "Optical performance improvements 2" described various embodiments, where a complex multidimensional exploration discovered lens adjustment systems 100 with critically improved optical performances regarding vision improvements and refractive outcomes by a careful design of the most critical system factors. The present section focuses on evaluating the optical performance of the same systems, but from the viewpoint of controlling and preferably reducing the transmitted portion of the incident light. Improving this aspect of the optical performance can be useful, and in fact critical, to make sure that in cases when the optical system 140 is the human eye, the irradiance of the light transmitted by the light adjustable lens 130 stays well below exposure limits of the retina.

As described elsewhere in the application, some existing light adjustable lenses 130 include a UV absorber in the bulk of the light adjustable lens, and beyond that, they also include a highly absorbing UV back-layer, or blocking-layer, 310, shown in FIG. 4B, that serves to protect the retina from ambient sources of UV radiation and during the lock-in treatment.

After performing the irradiating step 230 to adjust a refractive property of the optical system 140 to achieve the optimum vision for a patient, the macromers that diffused from their initial location to a new location as a consequence of the irradiating step 230 in the implanted light adjustable lens 130, shall be locked-in, in other words, photo-polymerized n step 250, in order to prevent the light adjustable lens 130 from undergoing further refractive changes. The lock-in radiant exposure can be on the order of 10-20 times greater than a typical exposure used in the refractive adjustment step 230. It is important to reduce and sufficiently attenuate the irradiance of the incident UV light by the UV absorber in the bulk of the lens and by the UV absorbing back-layer 310 at the back of the lens in order to minimize the ocular, and in particular the retinal exposure during the locking-in step 250.

In order to determine the overall transmittance attenuation, spectral transmittance measurements were performed on light adjustable lenses using a series of spectral bandpasses and central peak wavelengths, as before. All spectral transmittance measurements were performed by fixturing a wet cell to the entrance aperture of a 6" integrating sphere (OL-IS-670, Gooch & Housego, Orlando, Fla.) fiber optically coupled (OL-730-7, Gooch & Housego, Orlando, Fla.) to a calibrated (NIST traceable), double grating spectroradiometer (OL-756, Gooch & Housego, Orlando, Fla.).

Figure 10B:
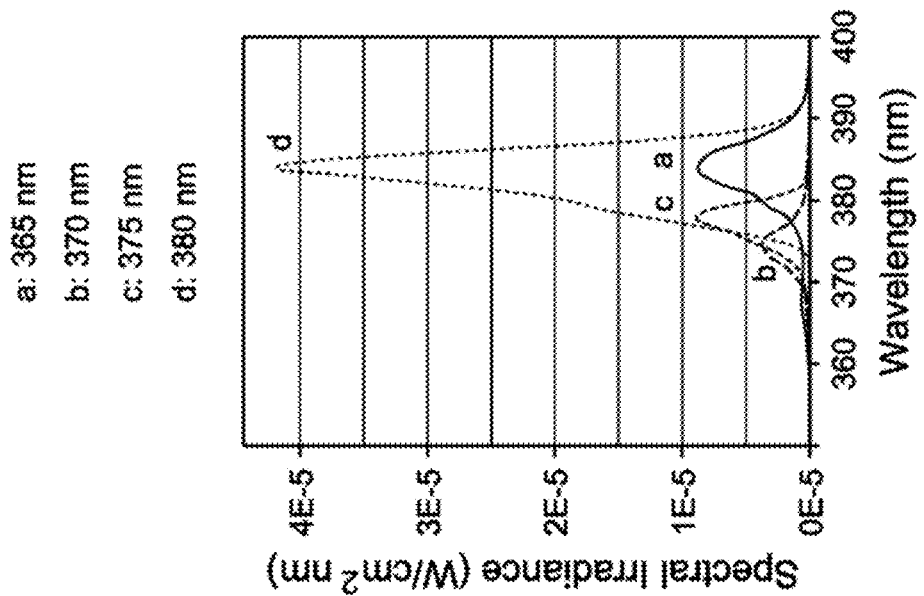
FIGS. 10A-B show the transmittance measurements with four light sources having different center wavelengths, performed with embodiments of existing light adjustable lenses.
Figure 10A:
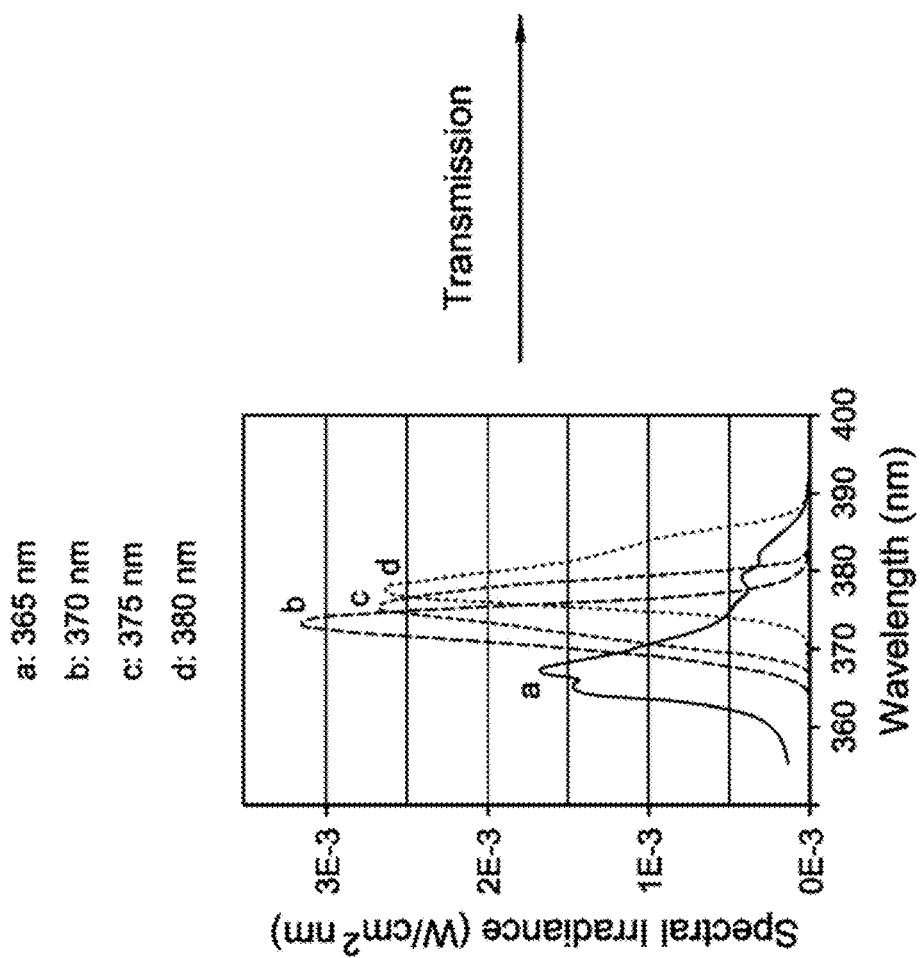

Results for a set of the light adjustable lenses are shown in FIGS. 10A-B, using four different spectral bandpasses and center wavelengths. FIG. 10A displays the spectral irradiance for each of the four center wavelengths incident on the anterior surface of the lenses. The areas under the four curves, i.e., the incident integrated spectral irradiance and power, were approximately identical for each of the four spectral bandpasses. FIG. 10B shows the spectral transmittance, or spectral irradiance after transmission, for each center wavelengths and bandpasses through these lenses. Integration of the spectrum of the transmitted light divided by the integrated spectrum of the light incident on the anterior surface of the lens is one of the measures that is used to characterize the transmission of the lens.

Table 7 provides a summary of the transmittance measurements. For ease of comparison, the transmittance of each spectral bandpass is displayed relative to that of the 365 nm filtered mercury arc source. Inspection of the ratios indicates that the spectral bandpasses with center wavelengths of 374 nm (FHWM=6 nm) and 377 nm (FWHM=6 nm) produce significantly less transmitted light than the 365 nm light source: a 70% and 37% transmission reduction was observed, respectively. In contrast, the spectral bandpass with a center wavelength of 380.5 nm (FWHM=8 nm) transmitted 269% more light compared to the mercury lamp with 365 nm wavelength.

TABLE 7

LAL spectral transmittance data with different spectral bandpasses.

| Central Wavelength (nm) | FWHM (nm) | Transmitance Ratio of Spectral Band Pass Relative to that of the Filtered Hg Arc Source |
|---|---|---|
| 367 | 9 | 1 |
| 374 | 6 | 0.3 |
| 377 | 6 | 0.67 |
| 380.5 | 8 | 3.69 |

Analysis of this transmittance data shows that embodiments of the light adjustable lenses exhibit a particularly efficient light attenuation for UV light with a center wavelength in the region of 374 nm-377 nm. This is yet another exploration of how to improve another critical optical performance factor with a judicious selection of a relevant figure of merit (in this case, the transmittance, directly related to the attenuation), followed by the careful analysis of the space of system factors how to improve this figure of merit.

Remarkably, it is recalled here that Tables 4A and 4B indicated that another figure of merit, the wavefront sag, that represented the simultaneous optimization of two other optical performance factors, also tended to be optimal in the 375-377 nm range (with FWHM=6 nm). Thus, the present analysis revealed that this 375-377 nm center wavelength range simultaneously maximized the wavefront sag, as well as maximized the light attenuation as well for this set of light adjustable lenses. Connecting the improvement of these two optical performance factors is an example of the complex multi-dimensional system design project.

As emphasized earlier, besides the identification and development of specific embodiments where a center wavelength and other system factors optimize several figures of merits simultaneously—representing an even larger number of competing optical performance factors—the complex, multidimensional method of determining these optimal system factors is itself also inventive, as described in steps (1)-(12) earlier.

Optical Performance Improvement 4

In addition to the dioptric power change and the spectral transmittance experiments, described in the previous three "Optical performance improvement" sections, a further optical performance factor is related to the question whether the optical performance factor improvements created by the inventive irradiating step 230, described in the previous three sections, are preserved even after the locking-in step 250 of method 200. The answer to this question is not obvious, since the locking-in step 250 "consumes" the residual macromers by photo-polymerizing them, as well as all the remaining photoinitiators, thus neutralizing them. Further, many of the responses to even modest changes in the system factors were found to be very non-linear and very amplified variations of the optical performance, the last example being the non-monotonic, rapid, and exponentionally strong rise of the transmittance when the light wavelength changes only by the minimal amount across 380 nm, as shown in Table 7.

To evaluate and improve the persistence of the adjustments of the optical performance factor, a series of lock-in irradiations were also performed on two sets of light adjustable lenses. The first group included existing LALs, where the irradiating UV light had the typical center wavelength of 365 nm. The other group consisted LALs optimized according to the previous three sections, and irradiated with the determined corresponding optimal spectral bandpass, or center wavelength, of 377 nm (FWHM=6 nm). These will be denoted as LAL' lenses.

Embodiments of these LAL' lenses involved a reduction of the concentration of UV absorber in bulk of the lens. In general, the UV absorbers typically have a concentration in the 0 wt % to 0.05 wt % range. Embodiments of some of the existing LALs have UV absorbers in concentrations of 0.04 wt % or higher. Embodiments of the LAL's have UV absorbers in reduced concentrations, below 0.04 wt %, such as in the 0.03 wt % to 0.04 wt % range. In some embodiments, the UV absorber concentration can be 0.03 wt %, in some embodiments, even less. With these choices, there will be less competition for the applied light between the UV absorber and the photoinitiator in the LAL' because of the reduced UV absorber in the bulk of the light adjustable lens.

Further, a new UV absorbing molecule UV12 was incorporated into the back layer 310 of the LAL' lenses, with an improved absorption coefficient. Embodiments of efficient UV absorbers, some used in a back-layer of a LAL' lens, such as the UV12 molecules, were described in the commonly owned U.S. Pat. No. 9,119,710, incorporated herein in its entirety by reference.

The next system factor to be optimized was the thickness and corresponding optical density of the back-layer 310. Increasing the thickness and the optical density of the back-layer 310 can reduce and minimize the retinal and ocular exposure, a high value optical performance factor. In some embodiments, the ultraviolet-absorbing back-layer 310 was chosen to have an optical density sufficiently high to reduce an irradiance of a transmitted portion of the lock-in radiation, transmitted by the light adjustable lens, to below an exposure limit of a human retina. In other embodiments, the back-layer had an optical density high enough to reduce the irradiance of the transmitted portion of the lock-in radiation to below one tenth of the exposure limit of a human retina.

As mentioned before, the locking-in irradiances were 10-30 times higher, in some cases about 20 times higher than the irradiances used in the irradiating steps 230 that were aimed at photo-polymerizing only a portion of the macromers.

Chemical extraction analysis of these two groups of locked-in lenses followed by comparison of their residual macromer and photoinitiator concentrations indicated that the optimized spectral bandpass for the LAL' lenses displayed a 34% and 20% improvement in photoinitiator and macromer polymerization efficiency, respectively.

Figure 11:
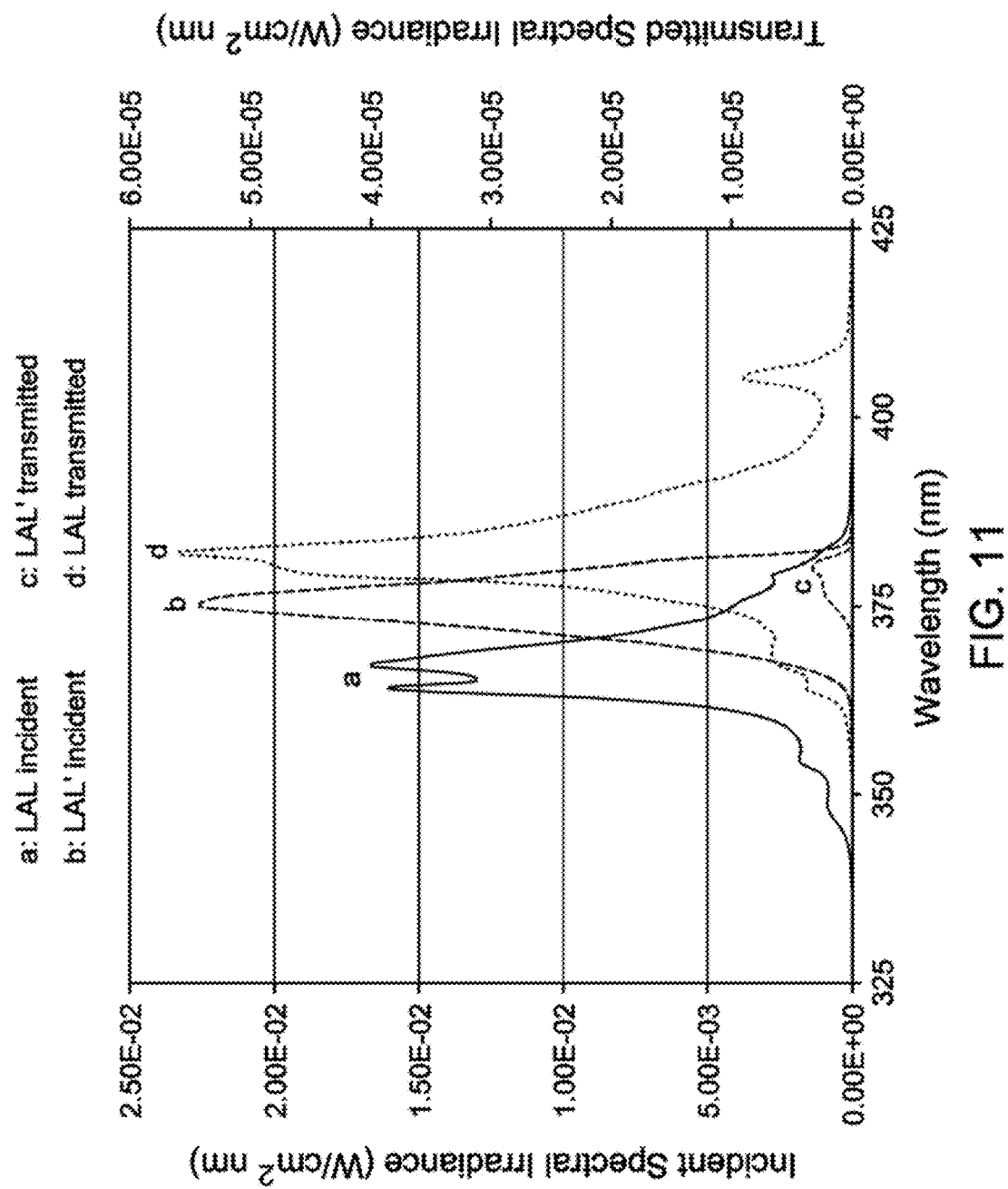
FIG. 11 shows the incident and transmitted spectral irradiances for existing LAL lenses, and for embodiments of the optimized LAL' lens. The transmitted irradiances are to be read off the vertical axis on the right.

FIG. 11 illustrates the results of some of the studies, comparing the optical performance of the LAL and the LAL' lenses. The incident spectral irradiances are to be read off from the left vertical axis, the transmitted irradiances from the right vertical axis. Overall, both lenses attenuated the irradiance greatly, as shown by the transmitted irradiances being approximately three orders of magnitude smaller than the incident irradiances. Beyond that, the LAL' lenses offered even further reduced transmittances, as shown by the amplitude of the (c) curve, representing the LAL' lenses to be much smaller than the amplitude of the (d) curve, representing the LAL lenses, for comparable incident irradiances. The cumulative effects of (1) reducing the concentration of the UV absorber in the bulk from above 0.04 wt % to the 0.03 wt % to 0.04 wt % range, in some cases to 0.03 wt %, and (2) increasing the absorption coefficient of the UV absorber in the back layer by employing a different absorption molecule, and (3) using a back-layer thickness and corresponding optical density in a suitably chosen range (described further above and below) in the LAL' lenses resulted in a reduction of the transmitted irradiance by a factor of 10-20 compared to the LAL lenses. Given that this transmitted irradiance directly controls the retinal exposure, a critical optical performance factor, making the attenuation stronger by such a large factor is a very useful gain.

The improvement of the efficiency of the UV blocking by the LAL' lenses in comparison to the LAL lenses can be represented in another manner by integrating the spectral irradiances over the entire UV spectrum. In some embodiments, the ratio of this spectrally integrated irradiance of the lens-transmitted portion of the ultraviolet light to the irradiance of the lens-incident ultraviolet light was less than 0.1% in the LAL' lenses. In some embodiments, this ratio was less than 0.02%. These very low transmitted irradiance values show that the LAL' lenses are attenuating the irradiation, including the locking-in irradiation, extremely efficiently, thus guaranteeing a very minimal, advantageous retinal exposure.

One could conclude that further increasing the thickness of the back-layer of the LAL' lenses would lead to even better attenuation. Remarkably, however, a competition of optical performance factors was again discovered by observing that the UV back-layer blocked the locking-in light so efficiently that a portion of the macromers inside the this back-layer did not polymerize even during the locking-in step 250 and thus remained mobile. Therefore, even after the entire method 200 concludes, these macromers could still diffuse into the bulk of the light adjustable lens 130, and possibly change its optical performance in an unplanned and possibly undesirable manner. This subsequent, potentially undesirable optical power change can be minimized by making the back-layer 310 thinner. Doing so, however, reduces its ability to attenuate the incident UV light. Again, a figure of merit was developed to simultaneously optimize these competing factors, one favoring thicker back-layers, the other, thinner back-layers. As a consequence, in some embodiments, the ultraviolet-absorbing back-layer 310 was chosen to be thin enough such that macromers in the ultraviolet-absorbing back-layer, not polymerized by the locking-in, are unable to cause a subsequent change of the dioptric power of the light adjustable lens in excess of 0.2 D.

Translating the above optical densities and these competing performance factors into thicknesses of the back-layer 310, in some embodiments, the ultraviolet-absorbing back-layer had a thickness of less than 100 microns. In other embodiments, the thickness was in the 30-70 microns range, such as 50 microns.

Light Source and Light Delivery System

In this final section, the light source 110 and the light delivery system 120 are described in some detail. In various embodiments, the UV light source 110 can generate a UV light having a center wavelength in range from 365 nm to 381 nm is used for modifying the power of a light adjustable lens. In some embodiments, the UV light has a center wavelength in the range from 370 nm to 379 nm. In some embodiments, the UV light has a center wavelength in range from 370 nm to 377 nm. When referring to the center wavelength, the term "about" can mean +/−0.5 nm.

Further, the UV light having a narrow full width half max spectral bandwidth (FWHM) can be also beneficial. Accordingly, a UV light with a narrow spectral band width is used in embodiments. For example, the UV light with a spectral bandwidth of +/−10 nm. In some embodiments, spectral bandwidth can range from 5 nm to 10 nm, e.g., the spectral bandwidth can be 5 nm, 6 nm, 7 nm, 8 nm, 9 nm or 10 nm. In some additional embodiments, spectral bandwidth can range from 2 nm to 8 nm, in some, from 6 nm to 8 nm. Several methods are known that can be used for achieving a desired narrow spectral bandwidth. For example, commercially available bandpass interference filters can be inserted in the beam of the UV light source.

Generally, any UV light source can be employed with embodiments of the present invention. For example, the UV light source can be a laser, light emitting diode, or various types of lamps that possess a UV spectrum. The source can also be continuous (CW) or pulsed. Specific embodiments provide UV light sources for irradiating light adjustable intraocular lenses. Useful sources include, but are not limited to, continuous wave (CW) UV sources such as CW LEDs, a CW laser, or an arc discharge lamp; pulsed UV lasers, and arc lamps. In one embodiment, an extended ultraviolet light (UV) source can be used, e.g., UV light emitting diodes (LED) for irradiating the lens. These exemplary UV light sources can be used with a desired spectral bandpass filter for conducting UV irradiation on light adjustable lenses. In some embodiments, the UV light source can be a continuous wave light emitting diode.

In some embodiments, the method 200 can further comprise measuring the aberrations of an optical system (e.g. the eye) containing the lens (including preexisting aberrations and those induced by the clinical procedure and wound healing) and aligning the source of the modifying the UV light so as to impinge the UV light onto the lens 130 in the spatially defined irradiance pattern 150 that will effectively null the aberrations. Controlling the irradiance and duration of the UV light controls the magnitude of the impinging radiation. The pattern can be controlled and monitored while the lens is irradiated.

There are many instruments available to measure aberrations in the eye. For example, the same instruments used to determine a patient's prescription for eyeglasses can be used. There are several instruments for measuring spherical and astigmatic refractive errors as well as higher order aberrations of the eye. One of the most common wavefront sensors used today is based on the Shack-Hartmann wavefront sensor. The instrument for measuring aberrations can be a stand-alone instrument or it can be built into the irradiation system. The diagnostics can be performed during irradiation more readily when the diagnostics are built into the irradiation system.

In some embodiments, a Shack Hartmann wavefront sensor is used to measure the aberrations in the eye; a nomogram of the light adjustable lens's response to irradiation is then consulted to determine the required spatial irradiance profile to correct the measured aberrations. This can be followed by the required irradiance profile being placed on a programmable mask generator, such as a digital mirror device. Next, a calibration camera can be used in a closed loop operation to correct the digital mirror device to compensate for aberrations in the projection optics and non-uniformity in the light source. Finally, the light adjustable lens can be radiated for a prescribed time period; after which the aberrations in the eye can be re-measured to ensure that the proper correction was made. If necessary, the process can be repeated until the correction is within acceptable or planned dioptric range. An exemplary use of a Shack-Hartmann wavefront sensor for measuring aberrations is described in FIG. 6 of U.S. Pat. No. 6,905,641.

In a particular example, the LAL is implanted in a patient's eye and the eye's refraction is allowed to stabilize post operatively. Aberration analysis is made of the patient's eye using standard refraction techniques, in some cases with a wavefront sensor. Using the knowledge of the eye's measured aberrations in conjunction with a previously derived nomogram permits the calculation of the desired irradiation profile and dosage to correct the patient's vision by correcting the LAL using variants of the method 200 disclosed herein.

Once the aberrations, or the deviations of the dioptric power from its planned values are corrected, the locking-in irradiation is applied in the step 250. The locking-in irradiation can be, but not necessarily, applied with the same irradiation system 110-120.

In various embodiments, modifying UV light is generated and projected onto the light adjustable lens 130 in a pattern or profile 150 that compensates for the aberration, for example, one that is opposite in phase to the measured aberrations. A beam intensity shaper can be used to generate a customized refraction change in the LAL. For example, optical lenses and/or apodizing filters can be used to form a customized pattern of irradiation to generate a customized refraction change in the LAL.

In some embodiments, the pattern of modifying light is obtained by use of an apodizing filter having a predetermined spatial irradiance profile. The apodized pattern can be generated using several methods and take different forms. For example, the desired transmission pattern could be a static mask pattern imaged onto photographic film, photochemically etched onto a substrate using a pattern generating machine, or chrome applied to the appropriate substrate using chemical vapor deposition (CVD). This type of static pattern can be either continuous or half tone structure. In addition, the desired pattern can be dynamic such as that produced by an appropriate spatial light modulator (SLM), such as a liquid crystal display (LCD) or a digital mirror device (DMD), rotating or translating patterns, or any other method to vary the irradiance profile or integration time of the exposed radiation dynamically. Some lasers are naturally apodized and may not require further intensity modulation for correcting power or astigmatism in a light adjustable lens. For example, a photographic film mask can also be used. In such embodiments, a photographic film can be placed between two glass slides to produce the 3-D intensity profile in a UV projection system similar to a conventional slide projector. The main components are a UV light source, condenser optics, a field lens, an apodizing filter, and projection optics.

In still other embodiments, a spatial light modulator (SLM) or digital mirror device (DMD) can be used. In any of these embodiments, the planned pattern or profile of light generated for the correction of the measured optical aberrations can be obtained or modified by the use of wavefront sensor feedback, for example from a Shack-Hartmann sensor. Such a sensor used in conjunction with a deformable mirror (DM) has been widely used to correct the aberrations of astronomical telescopes.

Another potential source for producing a spatially defined, variable irradiance pattern is a UV vertical cavity surface-emitting laser (VCSEL). In contrast to the use of static masks, or dynamic light modulators, such as an LCD or a DMD, a VCSEL array would only require a laser array, lens matrix array, and projection optics. Thus, the advantages can be lower cost and complexity. A controlled VCSEL 2-D array of lasers can replace a mask or an SLM. The VCSELs can be single element lasers, 1-D arrays, or 2-d arrays. Each laser element can emit a nearly square laser beam from the top surface in a narrow cone of light. Most of the research on these devices has been in the near IR for telecommunication applications. Some visible arrays have been developed for scanning and detecting images. The fill factor for 2-d arrays is usually small because of the space needed for the leads. However, lens arrays can be placed on top of the VCSEL arrays to obtain fill factors greater than 90%. These lasers have very high modulation frequencies. If it is too difficult to control the intensity of the lasers, the energy in the exposure can be controlled with pulse-width modulation or other modulation methods. By spatially controlling the intensity or average energy in each laser, one can produce an effective beam intensity profile. This pattern or profile 150 can then be imaged onto the LAL, or film, to produce the desired refraction pattern. The advantage is direct and instantaneous or nearly instantaneous control of the irradiation pattern and increased pattern combinations.

Since the same beam profile variation can be accomplished with various types of spatial light modulators and standard display or projection optics, the ramifications of the UV-VCSEL of this embodiment are in the simplicity and in the size of the packaging. These issues are more important when the irradiation system is combined with the wavefront sensor and some type of viewing and video capability. Use of UV-VCSELs for irradiating light adjustable lenses or films has been described, for example in, U.S. Pat. No. 6,905,641, incorporated herein by reference in its entirety.

Accordingly, in some embodiments, a UV vertical-cavity surface-emitting laser (VCSEL) array can be used to generate a UV intensity pattern and project it onto the surface of a LAL. Such an arrangement provides further advantages in that the optical system is smaller, lighter, more versatile in generating different irradiance patterns, and less complicated than other UV patterning systems. The optical efficiency is also higher than that of other systems. Such systems also produce less heat; and finally, the operating lifetime of these UV light sources tends to be longer.

Depending on the light adjustable lens formulation, exposure to light with the appropriate wavelength will cause the refraction modulation composition to diffuse into the irradiated volume, and produce a concomitant change in the refractive power of the lens. The majority of the change in power of the light adjustable lens is due to a change in the radius of curvature of the LAL. Although, it is possible that some localized change in refractive index could occur as well since the refractive index of a closed thermodynamic system such as a light adjustable lens is proportional to the number of particles per volume. For example, if the lens is irradiated with a spatial irradiance profile 150 as that shown in FIG. 7A, then the macromers in the irradiated region will polymerize producing a difference in chemical potential between the irradiated and unirradiated regions, effectively setting up a diffusion gradient between the irradiated and unirradiated regions. To reestablish thermodynamic equilibrium, the macromers of the refraction modulating composition in the unexposed region will diffuse towards the center, decreasing the radius of curvature, and therefore, increasing the lens's power.

If, on the other hand, the lens 130 is irradiated with a pattern as that shown in FIG. 7B, the macromers will diffuse out from the central part of the lens producing an effective decrease in lens power.

Both of these changes in the radius of curvature are not necessarily a linear function of the irradiation because of boundary conditions at the edge of the lens, non-uniform thickness across the lens, and, possibly, non-linear response of the lens material to the irradiation. The irradiation profile, amplitude, and exposure time must be tailored for each patient to produce the correct amount of change in the LAL. This includes spherical power change, astigmatism, spherical aberrations, and other aberrations. This is referred to as customized irradiation.

According to an embodiment, a spatial light modulator can be used to generate a customized spatial irradiance profile for a composition comprising a refraction modulating composition dispersed in a polymer matrix forming a lens, e.g., an IOL. The spatial light modulator can be a liquid crystal display (LCD) or a digital mirror device (DMD), as described above.

For example, electromagnetic irradiation in the UV, visible, or near infrared portions of the spectrum is easily projected onto the lens by using a projection system similar to the ones used in commercial video/computer projection systems. Nevertheless, these projectors use the LCD or DMD to replace the film used in the projectors. LCDs can operate in either transmission or reflection mode. Since they rotate the plane of polarization of the light, polarized light and an analyzer are incorporated into these optical systems.

The DMD is a pixilated, micromechanical spatial light modulator, formed monolithically on a silicon substrate. The DMD chips have individual micro mirrors that are ~14 μm square and are coated with a reflective aluminum coating.

The micro mirrors are arranged in a xy array, and the chips contain row drivers, column drivers, and timing circuitry. The addressing circuitry under each mirrored pixel is a memory cell that drives two electrodes under the mirror with complimentary voltages. Depending on the state of the memory cell (a "1" or "0") each mirror is electrostatically attracted by a combination of the bias and address voltages to one of the other address electrodes. Physically the mirror can rotate ±12 degrees. A "1" in the memory causes the mirror to rotate +12 degrees, while a "0" in the memory causes the mirror to rotate −12 degrees. A mirror rotated to +12 degrees reflects incoming light into the projection lens system and onto the LAL. When the mirror is rotated −12 degrees, the reflected light misses the projection lenses and instead it is typically directed to a beam dump.

The DMD operates in digital mode, i.e. on or off. However, an apparent analog or gray scale image can be produced with DMDs by controlling how long the individual mirrors or groups of mirrors are in the "on" (deflecting light into the projection lenses) or "off" (deflecting light out of the acceptance angle of the projection lenses) state. The operating frequency of DMDs, sometimes referred to as the dither rate, can be of the order of 60 kHz. Thus, a particular spatial irradiance profile can be defined with high resolution, programmed into the DMD, and then used to irradiate the LAL. Because of its digital nature, the DMD enables the delivery of precise, complex patterns to provide greater range and control over the LAL refractive adjustments.

In another embodiment, photographic plates or films can be used in a conventional film projection type of system to project an irradiation pattern onto the LAL. In such embodiments, each different irradiance profile is generated by separate, dedicated individual masks, to be placed in the beam path of the projection system.

By using a LCD or a DMD to generate customized irradiance profiles, the time and expense of making a customized photographic mask can be eliminated. Each customized irradiance profile can be generated on a computer screen and then programmed into the LCD or DMD projector. The variable pattern on the computer screen can be produced with an equation representing a 3-D image of the spatial irradiance pattern. The parameters of the equation can be varied by the user or the physician, using the patient's refraction and a nomogram. The physician can also make adjustments to the pattern and its representative equation based on his/her own experience. In one embodiment, one can use the patient's refraction plus a wavefront analysis system to calculate the shape of the spatial irradiance profile for customized irradiation of the LAL.

As an example, the procedure in this embodiment generally involves making an incision in the anterior lens capsule to remove the cataractous crystalline lens and implanting a LAL in its place. After wound healing and subsequent refractive stabilization, the aberrations of the eye are measured either by conventional refraction techniques (defocus and astigmatism), by wavefront analysis (defocus, astigmatism, coma, spherical, and other higher order aberrations), or corneal topographical maps (for higher order aberrations). Knowledge of the aberrations as well as their spatial distribution in the eye after post-surgical healing allows the patient's vision to be corrected by a nomogram representing the light adjustable lens' response to light of a particular wavelength, spatial irradiance profile, and duration.

After determination of the type, magnitude, and spatial distribution of the aberrations in the eye, this information is fed into a computer program that works in conjunction with the nomogram that outputs the correct spatial irradiance profile, output power, as well as the duration of the light exposure. The information of the required spatial irradiance profile is then fed into the DMD to control the individual mirrors that ultimately determine the output of the DMD or projection system and the pattern is projected onto the light adjustable lens. Once the LAL is irradiated and the diffusion of the refraction modulating composition to the exposed region has occurred, the eye can be analyzed again. If this refractive or wavefront analysis indicates that the LAL needs to be further modified, the above sequence of using the nomogram and the DMD pattern generator can be repeated. Once the aberrations have been corrected as desired, the lens is irradiated to lock-in the achieved refractive adjustments of the lens in step 250, effectively prohibiting further diffusion and subsequent refractive changes in the LAL.

In another embodiment, a DMD can be used for the purpose of generating an irradiance profile 150 for the UV irradiation of a LAL. A commercial digital light processor projector (such as sold by Infocus, Inc.) can be purchased, the optics and light source can be removed, and replaced with a UV light source and lens system. The optics and light source can be replaced with units suitable for irradiating test IOLs. Scripts can be generated for MatLab (commercial computer program for solving math problems and generating graphic images) or other graphics programs to view 3-D intensity profiles and 2-D intensity projections of those profiles. The computer can then be connected to the modified commercial projector and test LALs can be irradiated with the calculated profiles. Flat disks and lenses can be made from the light adjustable lens material and irradiated with various patterns, irradiance levels, and exposure times to generate one or more irradiation nomograms. Typical, average irradiance levels range from 1 to 50 mW/cm$^2$, in some cases 6 to 18 mW/cm$^2$. Typical exposure times range from 10 to 150 seconds. Patient's refraction data can be used with the nomograms for correcting the optical power and astigmatism in the LAL. For higher order aberrations, such as spherical aberrations and coma, a wavefront sensor can be utilized. Although more time consuming, standard refraction techniques can be used to measure spherical aberration.

A nomogram, in its simplest form, is an x-y plot, or response table, of dioptric power change plotted versus the applied radiant exposure. For spherical power correction, the nomogram can simply be a curve on an x-y plot.

In various embodiments, an irradiation system can comprise the following components: (1) irradiation source 110, (2) beam irradiance shaper, (3) beam delivery system 120, (4) alignment system, (5) calibration element, (6) diagnostic element, and (7) locking element. An exemplary irradiation system amenable to embodiments is described in U.S. Pat. No. 6,905,641, content of which is incorporated herein by reference.

The foregoing has outlined rather broadly the features and technical advantages of the present invention in order that the detailed description of the invention that follows may be better understood. The foregoing, and additional features and advantages of the invention will be described hereinafter, form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying Figures. It is to be expressly understood, however, that each of the Figures is provided for the purpose of illustration and description only and is not intended as a definition of the limits of the present invention.

Although embodiments of the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and/or steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A method for post-operatively adjusting the refractive power of a light adjustable intraocular lens (IOL) in a human eye, the method comprising:

providing a light adjustable intraocular lens (IOL) in a human eye, the light adjustable intraocular lens comprising photo-polymerizable macromers in a first polymer matrix, and a refraction-change zone having a radius;

providing an ultraviolet (UV) light source to generate an ultraviolet light;

irradiating the generated ultraviolet light with a light delivery system onto the light adjustable intraocular lens with a center wavelength and with a spatial irradiance profile to photo-polymerize said photo-polymerizable macromers to change a dioptric power of the human eye by changing a refraction of the light adjustable intraocular lens over said refraction-change zone, thereby causing a wavefront sag to be within 28% of its maximum over an ultraviolet spectrum, wherein the wavefront sag is calculated from the equation: Sag=$\Delta$(Dioptric Power)*$y^2$/2, where y is the radius of the refraction-change zone of the intraocular lens, and $\Delta$ (Dioptric Power) is the change in dioptric power from pre-irradiation to post irradiation, measured in units of 1/length; and locking-in the light adjustable intraocular lens by applying a lock-in radiation to photo-polymerize macromers that were not polymerized by the irradiating, wherein the irradiating includes irradiating the light adjustable lens to change its dioptric power to adjust at least one of a myopic power, a hyperopic power, an astigmatism and a spherical aberration, and a higher order aberration of the human eye, wherein the ultraviolet light is irradiated with an average irradiance in a range of 1 mW/cm$^2$ to 50 mW/cm$^2$, wherein the irradiated ultraviolet light has a center peak wavelength in a range of 366 nm to 381 nm, and wherein providing the light adjustable lens further comprises providing the light adjustable lens with an ultraviolet absorber dispersed in the first polymer matrix and an ultraviolet-absorbing back-layer formed in conjunction with a back surface of the light adjustable lens, the ultraviolet-absorbing back-layer having an optical density sufficiently high to reduce an irradiance of a transmitted portion of the lock-in radiation, transmitted by the light adjustable lens, to below an exposure limit of a human retina.

2. The method of claim 1, wherein:

the irradiated ultraviolet light has a full width half maximum (FWHM) spectral bandwidth that does not exceed 10 nm.

3. The method of claim 1, the irradiating comprising:

irradiating ultraviolet light of the ultraviolet light source with the light delivery system on the light adjustable lens with the center wavelength and with the spatial irradiance profile, thereby causing the wavefront sag to be within 18% of its maximum over the ultraviolet spectrum.

4. The method of claim 1, wherein:
the light adjustable lens includes an ultraviolet light absorber in a concentration in the 0 wt % to 0.05 wt % range in a bulk of the light adjustable lens.

5. The method of claim 4, wherein:
the light adjustable lens includes an ultraviolet light absorber in a concentration in the 0.3 wt % to 0.04 wt % range in a bulk of the light adjustable lens.

6. The method of claim 1, the providing the light adjustable lens comprising:
providing the light adjustable lens with the ultraviolet-absorbing back-layer that has an optical density high enough to reduce the irradiance of the transmitted portion of the lock-in radiation to below one tenth of the exposure limit of a human retina.

7. The method of claim 1, the providing the light adjustable lens comprising:
providing the light adjustable lens with an ultraviolet-absorbing back-layer that is thin enough such that macromers in the ultraviolet-absorbing back-layer, not polymerized by the locking-in, are unable to cause a subsequent change of the dioptric power of the light adjustable lens in excess of 0.2 D.

8. The method of claim 1, the providing the light adjustable lens comprising:
providing the light adjustable lens with an ultraviolet-absorbing back-layer with a thickness of less than 100 microns.

9. The method of claim 8, the providing the light adjustable lens comprising:
providing the light adjustable lens with an ultraviolet-absorbing back-layer with a thickness in the 30-70 microns range.

10. The method of claim 1, the providing the light adjustable lens comprising:
providing the light adjustable lens with an ultraviolet-absorbing back-layer with an optical density high enough that a ratio of an irradiance of a lens-transmitted portion of the ultraviolet light to an irradiance of the lens-incident ultraviolet light is less than 0.1%.

11. The method of claim 10, the providing the light adjustable lens comprising:
providing the light adjustable lens with an ultraviolet-absorbing back-layer thick enough that a ratio of the irradiance of a lens-transmitted portion of the ultraviolet light to the irradiance of the lens-incident ultraviolet light is less than 0.02%.

12. The method of claim 1, the irradiating comprising:
irradiating the light adjustable lens with ultraviolet light from the ultraviolet light source, with a center wavelength and with a spatial irradiance profile, to change the dioptric power of the optical system in the (−2D, +2D) range.

13. The method of claim 1, the irradiating comprising:
irradiating the light adjustable lens with ultraviolet light from the ultraviolet light source, with a center wavelength and with a spatial irradiance profile, to change a dioptric power of the light adjustable lens by changing a refraction of the light adjustable lens in a refraction-change zone with a radius in a 4.5 mm-6 mm range.

14. The method of claim 1, the providing an ultraviolet light source comprising:
providing one of a continuous wave light emitting diode and a pulsed light emitting diode.

15. The method of claim 1, the irradiating comprising:
generating the spatial irradiance profile of the ultraviolet light by reflecting the ultraviolet light from a digital mirror device.

16. The method of claim 1, the irradiating comprising:
irradiating the light adjustable lens with the spatial irradiance profile, wherein the spatial irradiance profile is determined using information obtained by photo-feedback.

17. The method of claim 1, the method comprising:
measuring at least one of an optical power and an aberration of the optical system before irradiating the light adjustable lens.

* * * * *